(12) United States Patent
Yoo et al.

(10) Patent No.: US 6,943,007 B2
(45) Date of Patent: Sep. 13, 2005

(54) **IMMUNO-STIMULATING POLYSACCHARIDE SUBSTANCE FROM *PHELLINUS* SPP. STRAIN AND USE THEREOF**

(75) Inventors: Ick-Dong Yoo, Taejon (KR); Soo-Muk Cho, Kyunggi-Do (KR); Byeung-Wook Park, Taejon (KR); Jae-Kuk Yoo, Taejon (KR); Nam-Doo Hong, Seoul (KR); Hwan-Mook Kim, Taejon (KR); Sang-Bae Han, Choongchungbuk-do (KR); Chang-Woo Lee, Taejon (KR)

(73) Assignee: Korea Institute of Science and Technology, Seoul (KR)

( * ) Notice: Subject to any disclaimer, the term of this patent is extended or adjusted under 35 U.S.C. 154(b) by 230 days.

(21) Appl. No.: 09/846,634

(22) Filed: May 1, 2001

(65) Prior Publication Data

US 2001/0046972 A1 Nov. 29, 2001

Related U.S. Application Data

(62) Division of application No. 09/221,261, filed on Dec. 28, 1998, now abandoned.

(30) Foreign Application Priority Data

Apr. 30, 1998 (KR) ............................................. 98-15617
Apr. 30, 1998 (KR) ............................................. 98-15618
Apr. 30, 1998 (KR) ............................................. 98-15619

(51) Int. Cl.$^7$ .......................... C12N 1/14; A01N 63/04; C12P 1/02; C12P 19/04
(52) U.S. Cl. ...................... 435/254.1; 435/911; 435/72; 435/171; 424/93.5
(58) Field of Search ............................. 435/254.1, 911, 435/72, 171; 424/93.5

(56) References Cited

U.S. PATENT DOCUMENTS

| 4,051,314 A | 9/1977 | Ohtsuka ......................... 536/1 |
| 4,145,415 A | 3/1979 | Sato |
| 4,207,312 A | 6/1980 | Fujii et al. ................... 424/180 |
| 4,877,777 A | * 10/1989 | DiLuzio ....................... 514/54 |
| 5,278,320 A | 1/1994 | Monaghan ................... 549/60 |

FOREIGN PATENT DOCUMENTS

| JP | 10-088188 | 9/1999 |
| KR | 97-15743 | * 4/1997 |

OTHER PUBLICATIONS

Lee et al. The Korean Jouranl of Mycology. Dec. 1995. vol. 23. No. 4, pp. 325–331.*
Han et al., Immunopharmacology 1999;41:157–164.
Song et al., Chem. Pharm. Bull. 1995;43(12):2105–2108.

* cited by examiner

*Primary Examiner*—Vera Afremova
(74) *Attorney, Agent, or Firm*—Darby & Darby

(57) ABSTRACT

There is disclosed novel *Phellinus linteus* Yoo. This mushroom is identified as novel as analyzed by restriction fragment length polymorphism and by microbiological features. A polysaccharide substance isolated from the fruiting bodies or mycelia the strain and other *Phellinus* spp. has an anticancer activity by inciting the cytotoxicity of T-cells and the antibody forming potency of B-cells. Also, the polysaccharide substance shows a potent activity against cancer metastasis. The polysaccharide substance, which can stimulate the immunity of the body, may be effective in the prophylaxis and treatment of immune-related diseases, such as cancers and AIDS, and in the study on the basic mechanism of the diseases.

5 Claims, 13 Drawing Sheets

●: GLUCOSE (g/l)

■: MYCELIA (g/l)

▲: Ph

○: UNTREATED
●: PRETREATED
■: POSTTREATED

○: UNTREATED

●: POLYSACCHARIDE - TREATED

□: 0.1mg/kg ADRIAMYCIN - TREATED

■: POLYSACCHARIDE/0.1mg/kg ADRIAMYCIN -TREATED

O: UNTREATED
●: POLYSACCHARIDE - TREATED
□: 0.3mg/kg ADRIAMYCIN - TREATED
■: POLYSACCHARIDE/0.3mg/kg ADRIAMYCIN -TREATED

○: UNTREATED

●: POLYSACCHARIDE - TREATED

□: ADRIAMYCIN - TREATED

O: POLYSACCHARIDE (B16)

□: POLYSACCHARIDE (NCl-H23)

●: ADRIAMYCIN (B16)

■: ADRIAMYCIN (NCl-H23)

IMMUNO-STIMULATING POLYSACCHARIDE SUBSTANCE FROM *PHELLINUS* SPP. STRAIN AND USE THEREOF

This application is a divisional application of Ser. No. 09/221,261 filed Dec. 28, 1998 which is now abandoned.

BACKGROUND OF THE INVENTION

1. Field of the Invention

The present invention relates to a strain belonging to genus *Phellinus*, a polysaccharide substance produced from the strain, and use of the polysaccharide substance. More particularly, the present invention relates to a novel *Phellinus* spp. strain, a novel polysaccharide substance produced therefrom, which shows potent immuno-stimulating activity, and use of the polysaccharide substance in the prophylaxis and treatment of immunity-related diseases, such as cancers and AIDS, and in their mechanism study.

2. Description of the Prior Art

Mushrooms, a kind of higher fungi, are heterotrophic; they take in organic nutrients from the outside through microscopically structured hyphae. In the biosphere, they play a role as a decomposer which degrade complex organic materials into simple inorganic forms and finally return them into nature. Of fungi, most typical mushrooms belong to Basidiomycetes which characteristically form basidia which each bears on its surface four exogenous basidiospores upon coming to maturity. The mushrooms are further classified into Hymenomycetes which actively release spores from exposed hymenia. Representative of Hymenomycetes are *Aphyllophorales* and *Agaricales*. *Ramaria botrytis*, *Hymenochaete yasudai Imaz.*, *Climancodon septentrionalis*, *Coriolus versicolor*, and *Canoderma applanatum* fall under the category of *Aphyllophorales* and *Pleurotus ostreatus*, *Lentinus edodes*, *Schizophyllum commune*, *Tricholoma mastsutake*, *Amanits muscaria*, and *Coprinus comatus* are placed within the category of *Agaricales*.

From times past, it has been known in Oriental herb medicine that many mushrooms belonging to *Aphyllophorales*, a kind of Basidomycetes, are therapeutically active against various diseases, especially, tumors. In Korea, they have been transmitted from generation to generation as herb medicines or folk medicines and, among the mushrooms, particularly, *Phellinus linteus*, belonging to the family Polyporaceae, has been regarded as an extremely precious medicine. *Phellinus linteus*, however, is a very rare species in nature, so that its fruiting body is very difficult to obtain. Further, isolation and artificial culture of the mycelium of *Phellinus linteus* are regarded almost impossible. Accordingly, advantage has not been actively taken of *Phellinus linteus* despite its being recognized as a therapeutically very effective agent against tumors.

For treating cancers, various methods including chemotherapy, radiotherapy and surgery are conventionally used. Effective as these therapies are for solid cancer, they are insufficient for the perfect conquest of caners. Particularly, they are helpless for metastatic tumors.

Usually, chemotherapy using anticancer agents, such as adriamycin, and radiotherapy cause serious side-effects. In order to attenuate the side-effects, such an anticancer agent would be administered at a reduced dose. In this case, however, the therapeutic effect of the chemical becomes poor. What is worse, cancer metastasis cannot be prevented even after taking chemotherapy in treating cancers. Thus, conventional chemotherapy is effective against the growth of cancers to an extent, but cannot completely cure cancers.

An alternative method is to utilize immunosuppressives, known as immunotherapy. Representative examples of the immunosuppressives are cytokines, such as interleukine-2, tumor necrosis factors, etc. Interleukine 2 shows superior therapeutic effects, particularly for cancer metastasis. When being applied for the human body, interleukine-2 is required to be used at such a large amount as to cause serious side-effects. Recent research on novel immuno-stimulating substances which are non-cytokines and show excellent activity against cancer without side-effect, has resulted in the development of Lentinan and OK-432.

For last few years, a new technology in which chemotherapy is used in combination with immunotherapy, known as immunochemotherapy, has been gathering strength. For instance, adriamycin and the immnuonoenhancements are co-administrated to the patients suffering from cancer, with the aim of enhancing the anticancer effects while reducing the side effects of the chemical.

No study on the microbiological and genetical characteristics of *Phellinus* spp. strains has been, to our knowledge, reported, thus far. Microorganisms, even if the same species, may be significantly different from each other in the kinds and amounts of the materials they produce as well as may show a large diversity in culture conditions, strain stability, and frequency of genetic variation. The first thing to do in researching the fungi, *Phellinus*, on their valuable products is to select the strains which can produce a large amount of the products and be cultured in broth in addition to being of low genetic variation. *Phellinus linteus* strains are very diverse and modified in morphology as observed with a microscope, so that they are difficult to identify. However, their classification has been practically dependent on the morphological discrimination under a microscope.

In recent, new DNA analysis methods have been developed for research in population genetics and phylogenetics. Over phenotype analysis methods, the DNA analysis methods have an advantage of being able to analyze genotypes on the basis of evolution rate and heredity tendency. Of them, a restriction fragment length polymorphism (hereinafter referred to as "RFLP") technique allows the mutation of base sequence to be inferred so as to analyze genotypes (Dowling et al. 1990, 1990. Nucleic acid II: Restriction site analysis. In: Molecular systematics ed by D. M. Hills and C. Moritz. P250–317. Sinauer Associates Press). Because nuclear DNA is too large to easily analyze, organella genomes are usually utilized for DNA analysis (White and Densmore, 1992 Mitochondrial DNA isolation. In: Molecular genetic analysis of populations: A practical approach. Ed by A. R. Hoelzel. P29–58. Oxford university press). Particularly, advantage is taken of mitochondrial DNA. Generally, mitochondrial DNA is smaller in size and faster in evolutionary change rate than nuclear DNA and experiences maternal haploid inheritance, so that mitochondrial DNA is extensively used for study on the genetic structure and history of a population. Particularly, the RFLP of mitochondrial DNA is utilized for the study on inter-species mutation (Foster et al., 1988. Estimation of relatedness between Phythophothora species by analysis of mitochondrial DNA. Mycologia 80:466–478)

SUMMARY OF THE INVENTION

Through the intensive and thorough research on *Phellinus* spp. strains utilizing the DNA analysis method, the present inventors have found that a novel polysaccharide substance which a *Phellinus* strain produces, has a potent immuno-stimulating activity.

Therefore, it is an object of the present invention to provide a *Phellinus* spp. strain which produces a novel polysaccharide substance of immuno-stimulating activity.

It is another object of the present invention to provide a novel polysaccharide substance which shows a potent immuno-stimulating activity against immune-related diseases.

It is a further object of the present invention to provide use of the polysaccharide substance as an immunotherapy agent or in the study on the basic mechanism of the diseases.

For achieving these objects, first, various *Phellinus* spp. strains were cultured and their total DNA were isolated by a SDS-phenol method. Of the total DNA, only mitochondrial DNA is obtained. The mitochondrial DNA was digested with restriction enzymes BAMHI, ClaI, EcoRl and Pvull, followed by electrophoresis on an agarose gel. The DNA relatedness among the *Phellinus* strains was analyzed according to the method of Nei and Li (1979). From the analytical data, a novel strain was found which forms new relatedness to other strains. This strain was named *Phellinus linteus Yoo* and deposited in the Korean Collection for Type Cultures, Korean Research Institute of Bioscience and Biotechnology (52 Oun Dong, Yusong, Daejon 305–333, Republic of Korea) on Nov. 17, 1997 (Deposition No. KCTC 0399BP). An investigation was made on the microbiological features of the KCTC 0399BP strain. A novel polysaccharide substance was isolated and purified from the fruiting bodies and mycelia of the novel strain and tested for immuno-stimulating activity. The immuno-stimulating polysaccharide substance was analyzed for its sugar units and composition, followed by the structural analysis of carbohydrate component. Similarly, other various *Phellinus spp.* strains were cultured and their fruiting bodies and mycelia were subjected to isolation and purification to give polysaccharide substances which were also of immuno-stimulating activity.

Animal tests were performed. The immuno-stimulating polysaccharide substances were administrated to mice into which cutaneous cancer cells were implanted to measure their anticancer activity. Also, when being co-administrated with chemicals, the polysaccharide substances were measured for their change in anticancer activity. The effect of the polysaccharide substance on the growth of human cancer cells was researched. To mice which were intravenously injected with cutaneous cancer cells at the tails, the polysaccharide substance was administrated, in order to investigate its influence on cancer metastasis. In the present invention, the anticancer activity of the polysaccharide substance was found to be different from that of anticancer chemicals in mechanism.

BRIEF DESCRIPTION OF THE DRAWINGS

The above and other objects and aspects of the invention will become apparent from the following description of embodiments with reference to the accompanying drawings in which.

DETAILED DESCRIPTION OF THE PREFERRED EMBODIMENTS

Figure 1:
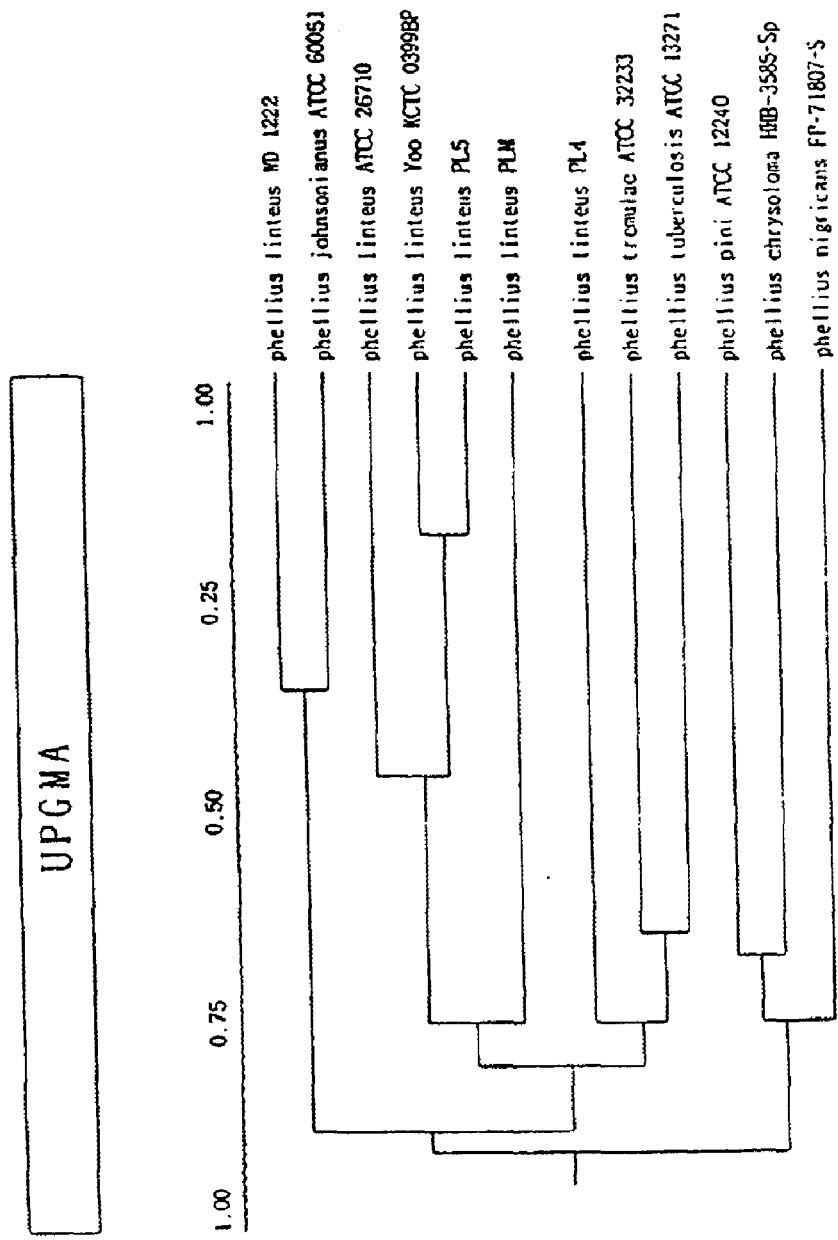
FIG. 1 is a phylogenetic tree showing the relatedness among *Phellinus* spp. strains.

13*Phellinus* strains including the novel *Phellinus linteus Yoo* KCTC 0399BP are each cultured on a potato dextrose agar (PDA). Using an SDS-phenol technique, a total DNA is isolated from the mycelia of each of the cultures, followed by further isolation of mitochondrial DNA from the total DNA. These mitochondrial DNAs are useful to analyze the relatedness among the strains. For this analysis, the mitochondrial DNAs are digested with restriction enzymes and the DNA fragments digested are separated on an agarose gel by electrophoresis. The distances which the DNA fragments move on the gel are the data for calculating restriction enzyme fragment relatedness values (F) and sequence divergence values (p). Based on the values, a novel strain was found with a relatedness and named "*Phellinus linteus Yoo*" and deposited in the Korean Collection for Type Culture, Korean Research Institute of Bioscience and Biotechnology (Deposition No. KCTC 0399BP). A study on the microbiological features of the fruiting body of *Phellinus linteus Yoo* KCTC 0399BP is helpful in proliferating this mushroom.

In order to extract the substance which is thought to be therapeutically effective, the mushroom is cultured and proliferated. A hot-water extraction gives a novel substance which is proved to be a kind of polysaccharides as analyzed by phenol-sulfuric acid and Folin-phenol techniques. In addition, the structural characteristics of this polysaccharide substance can be revealed by an NMR technique.

After being administrated to an animal, the polysaccharide substance is tested for immuno-stimulating activity by counting the number and measuring the proliferation of its lymphocytes. A similar procedure to that for *Phellinus linteus Yoo* is carried out for other *Phellinus* strains. That is, strain culture, mycelium extraction and substance isolation are sequentially done. The substances isolated are tested for Immuno-stimulating activity, too. In addition, the polysaccharide substances which are obtained from the fruiting bodies of the *Phellinus* strains are proved to be of immuno-stimulating activity.

In order to assay the activity of the polysaccharide substance against cancer, animal tests are performed. First, mouse-derived cutaneous cancer cells are implanted into mice to which the polysaccharide substance and other chemicals are, then, administrated alone or in combination. In either case, the viabilities of the mice are compared. The activity of the polysaccharide against human cancer is measured by using the nude mice into which human cancer cells are implanted. To the nude mice, the polysaccharide substance and adriamycin are administrated alone or in combination. In addition, the polysaccharide substance is very effective in preventing cancer metastasis. For this, mouse cutaneous cancer cells are intravenously injected into the tails of mice, followed by administration of the polysaccharide substance and adriamycin. A sulforhodamin B method is taken to measure viable mouse cutaneous cancer cells and human lung cancer cells which are previously treated with the polysaccharide substance and adriamycin alone or in combination.

A better understanding of the present invention may be obtained through the following examples which are set forth to illustrate, but are not to be construed as the limit of the present invention. In the following examples, splenocytes taken from $B_6C_3F$ mice were used for the measurement of the immuno-stimulating activity of the polysaccharide substances isolated from *Phellinus linteus Yoo* and other *Phellinus* spp. First, the splenocytes were immunized for 2 days by treatment with the substances and lipopolysaccharide as a positive control. The antibodies formed were measured by a spectrophotometer and considered as a standard for the immuno-stimulating activity. The effect of the polysaccharide substance on the proliferation of T-cells was measured by a mixed lymphocyte response technique. To detect the proliferation of lymphocytes, nuclear DNA which was newly synthesized in lymphocytes was measured by using $^3$H-thymidine.

EXAMPLE I

Culture of *Phellinus* Strain

The *Phellinus* spp. strains as given in Table 1, below, were each cultured on a potato dextrose agar (PDA) at a constant temperature of 28° C. for 5–12 days. Following inoculation in 450 mL of a PD broth, each of the strains was grown at 28° C. for 12 days with agitation at 120 rpm.

TABLE 1

*Phellinus* spp. used and Origins

| Strains | Origins |
| --- | --- |
| *P. linteus* WD1222 | Japan |
| *P. linteus* ATCC 26710 | U.S.A |
| *P. linteus* KCTC 0399BP | Korea |
| *P. linteus* PL5 | Korea |
| *P. linteus* PL4 | Korea |
| *P. linteus* PLM | Korea |
| *P. tremulae* ATCC 32233 | U.S.A |
| *P. johnsonianus* ATCC 60051 | U.S.A |
| *P. pini* ATCC 12240 | U.S.A |
| *P. tuberculosis* ATCC 13271 | U.S.A |
| *P. nigricans* FP-71807-S | U.S.A |
| *P. chrysoloma* HHB-3585-Sp | U.S.A |

EXAMPLE II

Total DNA Isolation

An SDS-phenol method was utilized for the Isolation of total DNA from mycelia. Each of the mycelia cultured in Example I was washed with 20 mM EDTA, harvested by vacuum filtration using a filter paper (Whatman No. 1), stored in a deep-freezer maintained at −70° C., and subjected to freeze-drying. The freeze-dried mycelia were finely ground and 2 g of each of these powders were added with 20 mL of an extraction buffer (0.2M Tris.HCl, pH 8.5; 0.25M NaCl; 25 mM EDTA; 0.5%(w/v) SDS) and then, with 14 mL of phenol and 6 mL of chloroform. After being mixed by slow agitation, the solution was centrifuged. The resulting supernatant was treated with 15 μl of RANase A (10 mg/mL) at 37° C. for 30 min. and then, further with 15 μl of proteinase K (10 mg/mL) at 60° C. for 15 min. Thereafter, the enzyme-treated supernatant was well mixed with an equal volume of a mixture of phenol, chloroform and isoamyl alcohol (25:24:1), followed by centrifugation at 12,000× g for 30 min. at 4° C. Before repeating the same centrifugation, the supernatant was well mixed with an equal volume of a mixture of chloroform and isoamyl alcohol (24:1). The supernatant thus obtained was mixed with 0.54 volume of isopropanol by voltexing and centrifuged under the same conditions as in above, to give a DNA pellet. This pellet was washed with 70% ethanol and dried in air. The DNA was dissolved in 8 mL of a TE buffer (10 mM Tris.HCl, 1 mM EDTA, pH 8.0) and stored at −20° C.

EXAMPLE III

Mitochondrial DNA Isolation

An ultracentrifugation was carried out to isolate mitochondrial DNA from the total DNA obtained from each of the strains in Example II. After being mixed with 8.8 g of cesium chloride, commercially available from Sigma, U.S.A., and 6 μl of a bisbenzimide solution (10 mg/mL), the total DNA solution (8 mL) was ultracentrifuged at 40,000× g for 40 hours at 20° C.

Following confirmation of two DNA bands under a uv light, only the upper band, that is, a mitochondrial DNA fraction, was recovered with the aid of a 21 gauge syringe needle. The mitochondrial DNA fraction thus obtained was added with an equal volume of CsCl-saturated isopropanol, mixed by weakly voltexing and centrifuged at 1,200× g at 4° C. This washing step was repeated 6–7 times so as to completely remove the bisbenzimide from the mitochondrial DNA fraction. Removal of the cesium chloride was accomplished by adding 70% ethanol three times in volume than that of the mitochondrial DNA fraction to the mitochondrial DNA and centrifuging at a speed of 100× g at 4° C. for 10 min. This washing step was repeated once more to give bisbenzimide- and Cs-free mitochondrial DNA. After being dried in air, the mitochondrial DNA was dissolved in a TE buffer (pH 8.0) and quantitated at 260 nm with a spectrophotometer, such as that sold by Beckman, U.S.A under the tradename of "DU-64 Spectrometer". The mitochondrial DNA was stored at −20° C.

EXAMPLE IV

Digestion of the Mitochondrial DNAs with Restriction Enzymes

The restriction enzymes used in the example as well as the buffers therefor were purchased from Boehringer Mannheim (Germany) and are given as listed in Table 2, below, along with their recognition sites. Each of the mitochondrial DNA samples of the *Phellinus* strains, obtained in Example III, had a concentration of 1 μg per 10 μl of buffer and digested at 37° C. for 3 hours.

TABLE 2

Restriction Enzymes and Their Recognition Sites

| Restriction Enz. | Recognition Sites |
|---|---|
| BamHI | G↓GATCC |
| ClaI | AT↓CGAT |
| EcoRI | G↓AATTC |
| PvuII | CAG↓CTG |

EXAMPLE V

Electrophoresis on Agarose Gel

The DNA samples which had been treated with the restriction enzymes in Example VI, were mixed with a gel loading buffer (0.25% bromophenol blue, 0.25% xylene cyanol FF, 30% glycerol) and electrophoresed on 1% agarose gel (agarose MP), sold by Boeringer Mannheim, Germany, for 4 hours in a horizontal electrophesing analyzer, commercially available from BRL, U.S.A., using a TAE buffer (40 mM Tris-acetate, 1 mM EDTA, pH 8.0) as a running buffer by applying 50 V across the analyzer. After running the DNA samples, the agarose gel was immersed in an ethidium bromide buffer (0.5 μg/mL in water) to easily detect the DNAs on a UV lamp. The mitochondrial DNA sizes which were determined by the electrophoresis are given as shown in Table 3, below.

TABLE 3

Sizes of Mitochondrial DNA Isolated from *Phellinus* spp.

| Strains | DNA Size |
|---|---|
| *P. linteus* WD1222 | 58 Kb |
| *P. linteus* ATCC 26710 | 59 Kb |
| *P. linteus* KCTC 0399BP | 61 Kb |
| *P. linteus* PL5 | 61 Kb |
| *P. linteus* PL4 | 73 Kb |
| *P. linteus* PLM | 63 Kb |
| *P. tremulae* ATCC 32233 | 77 Kb |
| *P. johnsonianus* ATCC 60051 | 76 Kb |
| *P. pini* ATCC 12240 | 76 Kb |
| *P. tuberculosis* ATCC 13271 | 57 Kb |
| *P. nigricans* FP-71807-S | 58 Kb |
| *P. chrysoloma* HHB-3585-Sp | 60 Kb |

EXAMPLE VI

Restriction Fragment Length Polymorphism (RFLP) Analysis

The analysis for the DNA relatedness between *Phellinus* strains was carried out according to Nei and Li method. Assuming that the DNA fragments were identical to each other if they moved the same distance when they were electrophoresed on agarose gel as in Example V, restriction enzyme fragment relatedness values (F) and sequence divergence values (p) were obtained. From the P values, the relatedness between *Phellinus linteus* Yoo (KCTC 0399BP) strain and other *Phellinus* spp. strains was analyzed by an Unweighted Pair-Group Method, arithmetic average (UPGMA) Clustering technique. The P and F values were calculated on the basis of the following equations, respectively:

$$F = 2n_{xy}/(n_x + n_y)$$

wherein F shows a relatedness between two *Phellinus* spp., $n_{xy}$ is the number of fragments in common therebetween, and $n_x$ and $n_y$ are each the total number of the fragments displayed by isolates x and y.

$$p = -(\ln F)/r$$

wherein p is an estimate of the proportion of nucleotide base substitution per nucleotide position and r is the number of the nucleotide base pairs for restriction endonuclease recognition site.

The F values obtained when treating with restriction enzyme BamHI are listed, together with their corresponding p values, in Table 4, the F values when treating with restriction enzyme ClaI, together with their corresponding p values in Table 5, the F values when treating with restriction enzyme EcoRI, together with their corresponding p values in Table 6, and the F values when treating with restriction enzyme PvuII, along with their corresponding p values in Table 7. Table 8 contains the proportions of the fragments in common and the arithmetic average distances corresponding to the p values listed over the diagonal line extending from the left above to the right bottom in each of the Tables 4–7. A phylogenetic tree was inferred from these results and is given as shown in FIG. 1, strongly suggesting that the strain of the present invention be newly differentiated from *Phellinus* strains with a significant relatedness.

TABLE 4

F and P values from PRLP of the BamHI-Digested Mitochondrial DNA

| | WD 1222 | ATCC 26710 | KCTC 0399BP | PL5 | PL4 | PLM | ATCC 32233 | ATCC 60051 | ATCC 12240 | ATCC 13271 | FP-71807-S | HHB-3585-Sp |
|---|---|---|---|---|---|---|---|---|---|---|---|---|
| WD1222 | — | | | | | | | 0.1921 | 0.4142 | | 0.3465 | 0.2310 |
| ATCC 26710 | NC | — | 0.0257 | 0.2570 | 0.3120 | 0.2841 | 0.2310 | | 0.2841 | 0.2203 | | |
| KCTC 0399BP | NC | 0.8571 | — | 0.0000 | 0.3120 | 0.2841 | 0.2310 | | 0.2841 | 0.3358 | | |
| PL5 | NC | 0.8571 | 1.0000 | — | 0.3120 | 0.2841 | 0.2310 | | 0.2841 | 0.3358 | | |
| PL4 | NC | 0.1538 | 0.1538 | 0.1538 | — | | 0.3358 | | | 0.3243 | | 0.3120 |
| PLM | NC | 0.1818 | 0.1818 | 0.1818 | NC | — | | | | | | 0.2841 |
| ATCC 32233 | NC | 0.2500 | 0.2500 | 0.2500 | 0.1333 | NC | — | 0.3753 | 0.2987 | 0.1735 | | 0.3465 |
| ATCC 60051 | 0.3158 | NC | NC | NC | NC | NC | 0.1052 | — | 0.4209 | 0.3666 | 0.2411 | 0.3567 |
| ATCC 12240 | 0.0833 | 0.1818 | 0.1818 | 0.1818 | NC | NC | 0.1666 | 0.0800 | — | 0.2915 | 0.3996 | 0.2165 |

TABLE 4-continued

F and P values from PRLP of the BamHI-Digested Mitochondrial DNA

| | WD 1222 | ATCC 26710 | KCTC 0399BP | PL5 | PL4 | PLM | ATCC 32233 | ATCC 60051 | ATCC 12240 | ATCC 13271 | FP-71807-S | HHB-3585-Sp |
|---|---|---|---|---|---|---|---|---|---|---|---|---|
| ATCC 13271 | NC | 0.2666 | 0.1313 | 0.1333 | 0.1428 | NC | 0.3530 | 0.1111 | 0.1739 | — | 0.2203 | |
| FP-71807-S | 0.1250 | NC | NC | NC | NC | NC | NC | 0.2353 | 0.0909 | 0.2666 | — | |
| HHB-3585-SP | 0.1250 | NC | NC | NC | 0.1538 | 0.1818 | 0.1250 | 0.1176 | 0.2727 | NC | NC | — |

TABLE 5

F and P values from PRLP of the ClaI-Digested Mitochondrial DNA

| | WD 1222 | ATCC 26710 | KCTC 0399BP | PL5 | PL4 | PLM | ATCC 32233 | ATCC 60051 | ATCC 12240 | ATCC 13271 | FP-71807-S | HHB-3585-Sp |
|---|---|---|---|---|---|---|---|---|---|---|---|---|
| WD1222 | — | 0.1155 | 0.1351 | 0.1527 | 0.2841 | 0.2987 | 0.3243 | 0.0372 | 0.1412 | | 0.2310 | 0.2507 |
| ATCC 26710 | 0.5000 | — | 0.0196 | 0.0851 | 0.1686 | 0.1831 | 0.2088 | 0.1527 | | | 0.1155 | 0.2570 |
| KCTC 0399BP | 0.4444 | 0.8888 | — | 0.0531 | 0.1831 | 0.1288 | 0.2203 | 0.1686 | | | 0.1351 | 0.2682 |
| PL5 | 0.4000 | 0.6000 | 0.7272 | — | 0.1964 | 0.1412 | 0.3465 | 0.1831 | | 0.1527 | 0.2841 | |
| PL4 | 0.1818 | 0.3636 | 0.3333 | 0.3077 | — | 0.1047 | 0.2411 | 0.1964 | 0.1736 | 0.1256 | 0.1686 | 0.2987 |
| PLM | 0.1666 | 0.3333 | 0.4615 | 0.4285 | 0.5333 | — | 0.3666 | 0.3243 | 0.1831 | 0.1831 | 0.1831 | 0.3120 |
| ATCC 32233 | 0.1428 | 0.2587 | 0.2666 | 0.1250 | 0.2353 | 0.1111 | — | 0.2310 | 0.2006 | 0.2006 | 0.2088 | 0.2203 |
| ATCC 60051 | 0.8000 | 0.4000 | 0.3636 | 0.3333 | 0.3077 | 0.1428 | 0.2500 | — | | 0.3465 | 0.1682 | 0.2841 |
| ATCC 12240 | 0.4285 | NC | NC | NC | 0.3529 | 0.3333 | 0.3000 | NC | — | 0.2682 | 0.3243 | 0.2203 |
| ATCC 13271 | NC | NC | NC | NC | 0.4706 | 0.3333 | 0.3000 | 0.1250 | 0.2000 | — | 0.3243 | |
| FP-71807-S | 0.2500 | 0.5000 | 0.4444 | 0.4000 | 0.3636 | 0.3333 | 0.2857 | 0.2000 | 0.1428 | 0.1482 | — | 0.2507 |
| HHB-3585-Sp | 0.2222 | 0.2222 | 0.2000 | 0.1818 | 0.1666 | 0.1538 | 0.2666 | 0.1818 | 0.2666 | NC | 0.2222 | — |

TABLE 6

F and P values from PRLP of the EcoRI-Digested Mitochondrial DNA

| | WD 1222 | ATCC 26710 | KCTC 0399BP | PL5 | PL4 | PLM | ATCC 32233 | ATCC 60051 | ATCC 12240 | ATCC 13271 | FP-71807-S | HHB-3585-SP |
|---|---|---|---|---|---|---|---|---|---|---|---|---|
| WD1222 | — | 0.3837 | 0.1921 | 0.2006 | 0.2764 | 0.2597 | 0.3302 | 0.0175 | 0.4339 | 0.1899 | 0.4071 | 0.2987 |
| ATCC 26710 | 0.1000 | — | 0.1442 | 0.2006 | 0.1608 | 0.2597 | 0.3302 | 0.3837 | 0.3183 | 0.3054 | 0.4071 | 0.4142 |
| KCTC 0399BP | 0.3158 | 0.4210 | — | 0.0509 | 0.2006 | 0.2507 | 0.2567 | 0.4275 | 0.3120 | 0.2310 | 0.2165 | 0.2915 |
| PL5 | 0.3000 | 0.3000 | 0.7368 | — | 0.2764 | 0.2597 | 0.1470 | 0.2682 | 0.3183 | 0.2378 | 0.2240 | 0.2987 |
| PL4 | 0.1904 | 0.3809 | 0.3000 | 0.1904 | — | 0.3837 | 0.2682 | 0.2764 | 0.4399 | 0.3120 | 0.2987 | 0.3054 |
| PLM | 0.2105 | 0.2105 | 0.2222 | 0.2105 | 0.1000 | — | 0.3243 | 0.2597 | 0.3120 | 0.4142 | | 0.1964 |
| ATCC 32233 | 0.1397 | 0.1379 | 0.2143 | 0.4138 | 0.2000 | 0.1428 | — | 0.3302 | 0.3662 | 0.1256 | 0.3465 | 0.2362 |
| ATCC 60051 | 0.9000 | 0.1000 | 0.0769 | 0.20000 | 0.1904 | 0.2105 | 0.1379 | — | 0.4339 | 0.2738 | 0.2915 | 0.4142 |
| ATCC 12240 | 0.0740 | 0.1481 | 0.1538 | 0.1481 | 0.0714 | 0.1538 | 0.1111 | 0.0740 | — | 0.3465 | 0.2203 | 0.2737 |
| ATCC 13271 | 0.3200 | 0.1600 | 0.2500 | 0.2400 | 0.1538 | 0.0833 | 0.4705 | 0.2400 | 0.1250 | — | 0.2568 | 0.2915 |
| FP-71807-S | 0.0869 | 0.0869 | 0.2727 | 0.2680 | 0.1666 | NC | 0.1250 | 0.1739 | 0.2666 | 0.2142 | — | 0.4339 |

TABLE 6-continued

F and P values from PRLP of the EcoRI-Digested Mitochondrial DNA

| | WD 1222 | ATCC 26710 | KCTC 0399BP | PL5 | PL4 | PLM | ATCC 32233 | ATCC 60051 | ATCC 12240 | ATCC 13271 | FP-71807-S | HHB-3585-SP |
|---|---|---|---|---|---|---|---|---|---|---|---|---|
| HHB-3585-SP | 0.1666 | 0.0833 | 0.1739 | 0.1666 | 0.1600 | 0.3077 | 0.2424 | 0.0833 | 0.1935 | 0.1379 | 0.0740 | — |

TABLE 7

F and P values from PRLP of the PvuII-Digested Mitochondrial DNA

| | WD 1222 | ATCC 26710 | KCTC 399BP | PL5 | PL4 | PLM | ATCC 32233 | ATCC 60051 | ATCC 12240 | ATCC 13271 | FP-71807-S | HHB-3585-SP |
|---|---|---|---|---|---|---|---|---|---|---|---|---|
| WD1222 | — | 0.2507 | | | | 0.2682 | 0.2411 | 0.0851 | 0.3567 | 0.2987 | 0.3358 | 0.3465 |
| ATCC 26710 | 0.2222 | — | 0.1155 | 0.1155 | 0.2987 | 0.2507 | 0.3465 | | 0.3465 | | 0.3243 | |
| KCTC 0399BP | NC | 0.5000 | — | 0.0479 | | | | | 0.3465 | | 0.3243 | |
| PL5 | NC | 0.5000 | 0.7500 | — | | | | | 0.3465 | | | |
| PL4 | NC | 0.1666 | NC | NC | — | 0.1968 | 0.2682 | | | 0.3358 | | |
| PLM | 0.2000 | 0.2222 | NC | NC | 0.3070 | — | 0.3567 | 0.2682 | | | | |
| ATCC 32233 | 0.2353 | 0.1250 | NC | NC | 0.2000 | 0.1176 | — | | 0.2310 | | 0.3996 | 0.4071 |
| ATCC 60051 | 0.6000 | NC | NC | NC | NC | 0.2000 | NC | — | 0.567 | 0.2987 | 0.3358 | 0.3465 |
| ATCC 12240 | 0.1176 | 0.1250 | 0.1250 | 0.1250 | NC | NC | 0.2500 | 0.1176 | — | 0.2597 | 0.1010 | 0.1760 |
| ATCC 13271 | 0.1666 | NC | NC | NC | 0.1333 | NC | NC | 0.1666 | 0.2105 | — | 0.1256 | 0.2507 |
| FP-71807-S | 0.1333 | 0.1428 | 0.1428 | NC | NC | NC | 0.0909 | 0.1333 | 0.5454 | 0.4706 | — | 0.2088 |
| HHB-3585-SP | 0.1250 | NC | NC | NC | NC | NC | 0.0869 | 0.1250 | 0.3478 | 0.2222 | 0.2857 | — |

TABLE 8

Proportions of fragments in common & arithmetic average distances corresponding to the p values

| | WD 1222 | ATCC 26710 | KCTC 399BP | PL5 | PL4 | PLM | ATCC 32233 | ATCC 60051 | ATCC 12240 | ATCC 13271 | FP-71807-S | HHB-3585-SP |
|---|---|---|---|---|---|---|---|---|---|---|---|---|
| WD1222 | — | 4/53 | 5/53 | 5/55 | 3/60 | 4/54 | 5/78 | 19/59 | 6/82 | 5/68 | 5/62 | 6/65 |
| ATCC 26710 | 0.2499 | — | 16/50 | 14/52 | 8/60 | 6/51 | 7/75 | 3/56 | 5/79 | 4/65 | 4/59 | 2/62 |
| KCTC 0399BP | 0.1636 | 0.0762 | — | 21/52 | 6/57 | 6/51 | 7/75 | 3/56 | 5/79 | 4/65 | 6/59 | 3/62 |
| PL5 | 0.1766 | 0.1645 | 0.0379 | — | 5/59 | 6/51 | 9/77 | 4/58 | 5/81 | 4/67 | 5/61 | 3/64 |
| PL4 | 0.2802 | 0.2350 | 0.2393 | 0.2616 | — | 7/58 | 8/82 | 4/63 | 4/86 | 8/72 | 4/66 | 4/69 |
| PLM | 0.2755 | 0.2444 | 0.2212 | 0.2283 | 0.2284 | — | 4/76 | 4/57 | 5/80 | 4/66 | 2/60 | 6/63 |
| ATCC 32233 | 0.2985 | 0.2791 | 0.2360 | 0.2415 | 0.2783 | 0.3490 | — | 5/81 | 10/104 | 14/90 | 5/74 | 8/87 |
| ATCC 60051 | 0.0823 | 0.2682 | 0.2980 | 0.225 | 0.2364 | 0.2840 | 0.3121 | — | 3/85 | 6/71 | 6/65 | 4/68 |
| ATCC 12240 | 0.3365 | 0.3163 | 0.3142 | 0.3163 | 0.3067 | 0.2475 | 0.2741 | 0.4038 | — | 6/94 | 12/88 | 12/91 |
| ATCC 13271 | 0.2443 | 0.2628 | 0.2834 | 0.2868 | 0.2744 | 0.2986 | 0.1665 | 0.3123 | 0.2914 | — | 10/74 | 4/77 |
| FP-71807-S | 0.3301 | 0.2823 | 0.2253 | 0.1883 | 0.2336 | 0.1831 | 0.3183 | 0.2591 | 0.2613 | 0.2317 | — | 5/71 |
| HHB-3585-SP | 0.3817 | 0.3324 | 0.2498 | 0.2914 | 0.3053 | 0.2641 | 0.3025 | 0.3503 | 0.2216 | 0.2711 | 0.2978 | — |

EXAMPLE VII

Microbiological Features of *Phellinus linteus Yoo* Strain KCTC 0399BP

The strain, *Phellinus linteus Yoo* KCTC 0399BP, which was identified as a novel strain newly differentiated from *Phellinus* with a great relatedness, was studied on its microbiological features. Its fruiting body, germless and perennial, had a woody part with a semi-circular pileus about 10 cm wide and about 4 cm thick. At the time of being picked, this mushroom had a dark brown surface, but, with the lapse of time, the surface came to have many fissures thereon and the color became deeper to black brown while its hymenial layer was changed in color from fresh red to yellowish brown. The tube of the hymenial layer had a multilayer structure with a fine pore rounded. Its spore 3–4 cm in length was subglobose and light yellowish brown-colored. Also, it had many setae and a chlamido in a dimension of 15–30×8–10 $\mu$m. The strain of the present invention was found to be identical in almost all aspects to the *Phellinus linteus* written in "Colored Illustrations of Mushrooms of Japan", p 189, printed by Hoikusha Imazeki, edited by Imazeki, R. and Hongo, T., and named *Phellinus linteus Yoo*. We deposited this novel strain to Korean Collection for Type Cultures, Korean Research Institute of Bioscience and Biotechnology, on Nov. 17, 1997, and received a deposition No. KCTC 0399BP.

EXAMPLE VIII

Culture of *Phellinus linteus Yoo* KCTC 0399BP

Figure 2:
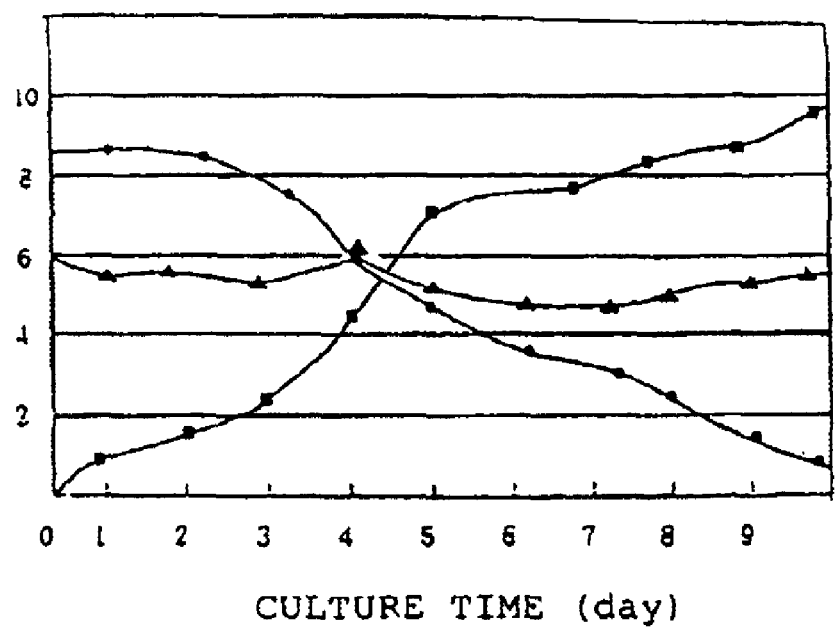
FIG. 2 is a graph showing the culture properties of the mycelia of *Phellinus linteus;*
Figure 3:
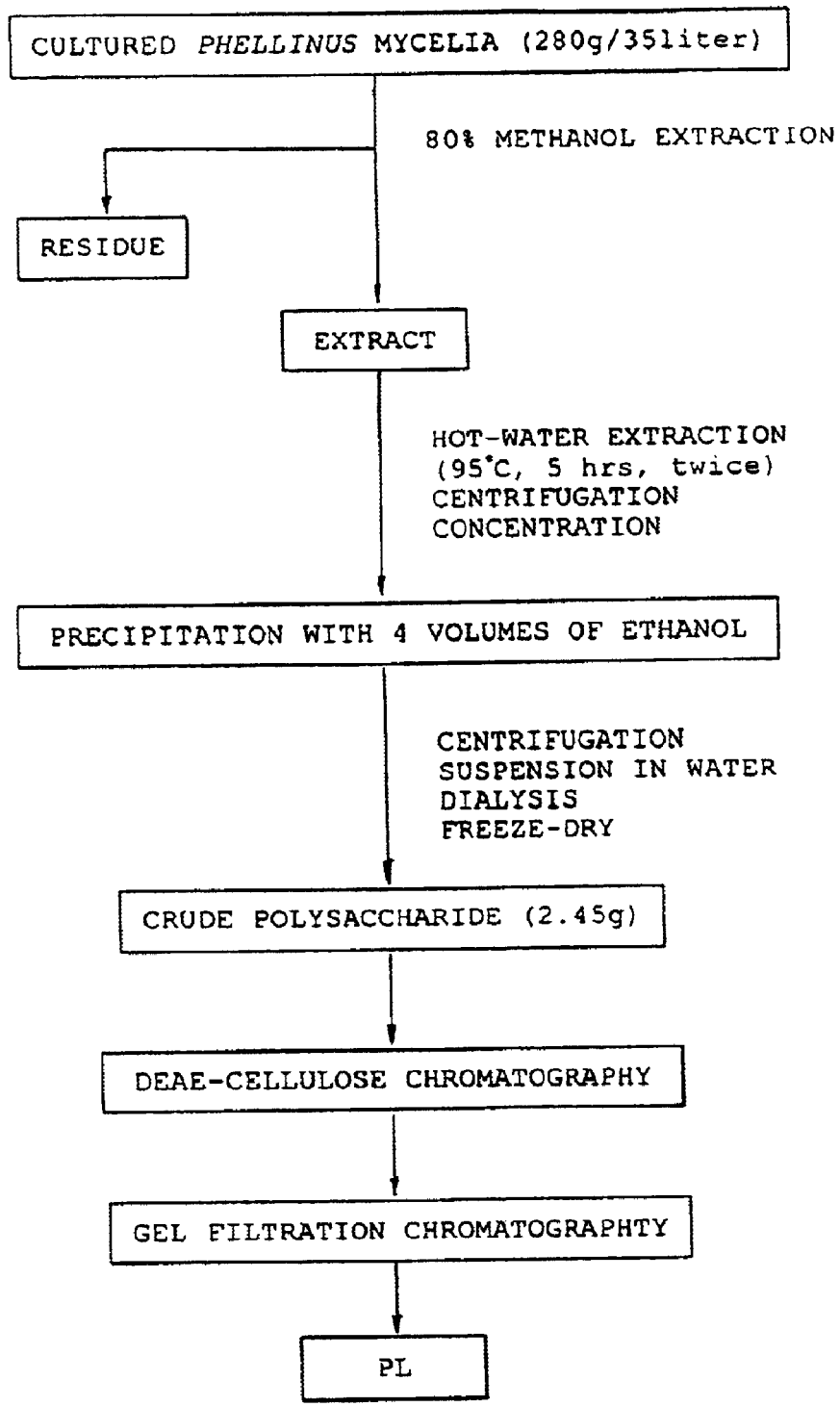
FIG. 3 is a procedure showing the purification of the polysaccharide substance from *Phellinus* stains.

A culture broth containing starch 50 g, peptone 10 g and yeast extract 10 g per distilled water 1 L, supplemented with $KH_2PO_4$ 0.8 g, $MgSO_4 \cdot 7H_2O$ 0.5 g and $CaCl_2$ 0.3 g, was adjusted to pH 6.0 and autoclaved. The mycelia of *Phellinus linteus Yoo* KCTC 0399BP were inoculated in 3.5 liters of the culture broth in a 5 liter fermentation bath and cultured at 28° C. for 11 days while aerating the broth at 2 vvm and rotating the bath at 160 rpm. At 5 days after culture, the highest yield for mycelia (30 g/l) was obtained, as shown in FIG. 2. From the mycelia cultured for 5 days, polysaccharide substances were hot water-extracted at a yield of 0.873% per weight of dried mycelia.

TABLE 9

Production Yields for Mycelia of *P. linteus* and Polysaccharide

| Items | Mycelia of 5 day-Cultured *P. linteus* |
|---|---|
| Dried Mycelia Wt. (g/L) | 30 |
| Dried Crude Polysaccharide Wt. | 262 |
| Crude Polysaccharide Yield (%) | 0.873 |

EXAMPLE IX

Extraction of Mycelium Culture of *Phellinus linteus Yoo* Strain

An extraction and purification process was done on a mycelium culture of *Phellinus linteus Yoo* strain, in order to obtain crude immuno-stimulating substances. First, 280 g of the mycelium culture obtained in Example VIII was subjected to hot water extraction, followed by concentration to give 3 g of a hot-water extract. This extract was added with ethanol to a final concentration of 80%, allowed to stand at 4° C. for 24 hours, and centrifuged. The pellet was dissolved in water and then, dialyzed 10° C. for 72 hours using a cellulose tube, such as that sold by Nippon Junko Jun Yaku Seihing, while the dialyzing solution was refreshed every 12 hours. The solution in the cellulose tube was freeze-dried to give a crude extract of 2.45 g.

EXAMPLE X

Isolation of Pure Immuno-Stimulating Substance

Purification was achieved by carrying out ion exchange chromatography and gel filtration chromatography successively.

First, the crude extract obtained in Example IX was dissolved in a 5 mM sodium phosphate buffer (pH 7.2), loaded on a DEAE-cellulose column and washed with the same buffer. A solution of NaCl in the same buffer having a concentration gradient from 0 to 1M was used as an eluting buffer. It was flowed through the column at a rate of 5 mL/min. and the eluate was collected at 15 mL per test tube. The eluted fractions were measured with respect to sugar content by a phenol-sulfuric method and with respect to protein content by Bradford's method. The fractions containing sugar were applied to the top of a column consisting of porous beads, such as that sold under the trade name of Toyopearl HW 65F, and further purified by gel filtration chromatography eluting with water, to afford a pure active fraction which was homogeneous in molecular weight and properties. Its sugar and protein content were measured by the same methods as in above. The pure immuno-stimulating substance thus obtained was named "PL".

EXAMPLE XI

Immuno-Stimulating Activity of the Polysaccharide Substance

The polysaccharide substance derived from Basidomycetes are known to have a positive influence on the proliferation or activity of lymphocytes, thereby increasing immunity against external factors and even cancer cells. This function of the polysaccharide substance is not attributed to direct cytotoxicity but results from immunological enhancement, so that they advantageously produce little side-effects in vivo. That is, the polysaccharide substances of Basidomycetes induce an enhancement in the cytotoxic function and antibody formation of the lymphocytes, B-cells and T-cells, thereby showing a potent anticancer immunoactivity. Therefore, the polysaccharide substances can be indirectly proved to be of anticancer immunoactivity by counting the number of anti-forming lymphocytes and measuring the proliferation of T-cells.

In this example, B-cells were counted by use of an antibody-forming cell method and the proliferation of T-cells was measured by a mixed lymphocyte response technique. In addition, in order to detect the effect of the polysaccharide substance on the proliferation of lymphocytes, the nuclear DNA which was newly synthesized was measured by using $^3$H-thymidine. The results are given in Table 10, below.

TABLE 10

Immuno-Stimulating Activity of various Substances

| Substance | Lymphocyte Proliferation effect (DPM × 10⁴) | T-Cell Activity (DPM × 10⁴) | B-Cell Antibody-forming (Abs 576 nm) |
|---|---|---|---|
| P. linleus Yoo | 8.4 ± 0.5 | 2.5 ± 0.1 | 0.66 ± 0.01 |
| LPS | — | — | 0.81 ± 0.23 |
| Control | 1.6 ± 0.5 | 0.5 ± 0.05 | 0.00 ± 0.00 |

*each substance was used at a concentration of 10 µg/mL.

As apparent from the data of Table 10, the polysaccharide substance extracted from the novel *Phellinus* strain of the present invention are superior to the control in lymphocyte proliferation and T-cell activity, both, by the factor of about 5-fold. The polysaccharide substance of the present invention show a high B-cell antibody forming power similar to that of lipopolysaccharide. Lipopolysaccharide is a very potent immunosuppressive agent but cannot be freely used owing to its serious side-effects in vivo.

EXAMPLE XII

Sugar Unit and Composition of the Immuno-Stimulating Polysaccharide Substance

Figure 4:
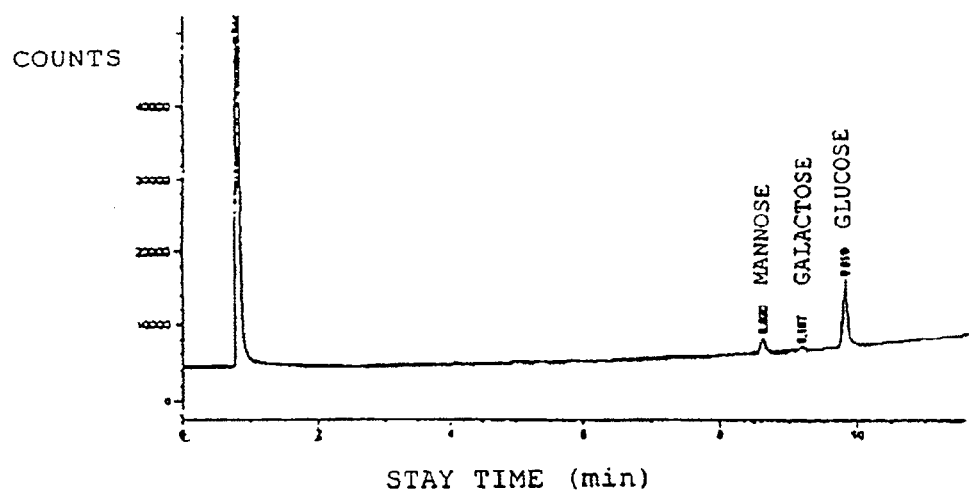
FIG. 4 is a gas chromatogram for the sugar units of the immuno-stimulating polysaccharide substance.

The polysaccharide substance obtained from Example X was subjected to gas chromatography to analyze its sugar units (FIG. 4). A phenol-sulfuric acid method and a Folin-phenol method were taken to measure its carbohydrate and protein components, respectively. The analysis carried out in an apparatus, commercially available from Hewlett Packard, identified as "HP 5890 GC", provided with a fused silica capillary column sp-2330 (0.32 mm×30 m) under the following conditions. The column was first maintained at 200° C. for 2 min. and heated at an elevation rate of 4° C. per min. to 250° C. which was, then, maintained for 2 min. A detector and a injector, provided to the apparatus, were maintained at 260° C. and 250° C., respectively. 2 mg was taken from each of the extract fractions obtained in Example XI, hydrolyzed with 2N TFA, reduced with $NaBH_4$ and acetylated with anhydrous acetic acid to give aditol acetate for use in gas chromatography. The results are given in Table 11, below.

TABLE 11

Sugar Units and Composition of the Immuno-Active Fraction

| Polysaccharide Extract | Carbo-hydrate (%) | Protein (%) | Sugar Units (mole %) | | |
|---|---|---|---|---|---|
| | | | Glucose | Mannose | Galactose |
| PL | 82.7 | 17.3 | 78.6 | 18.0 | 3.4 |

EXAMPLE XIII

Structural Analysis of the Immuno-Stimulating Polysaccharide Substance

The Immuno-stimulating polysaccharide substance was subjected to structural analysis.

Figure 5:
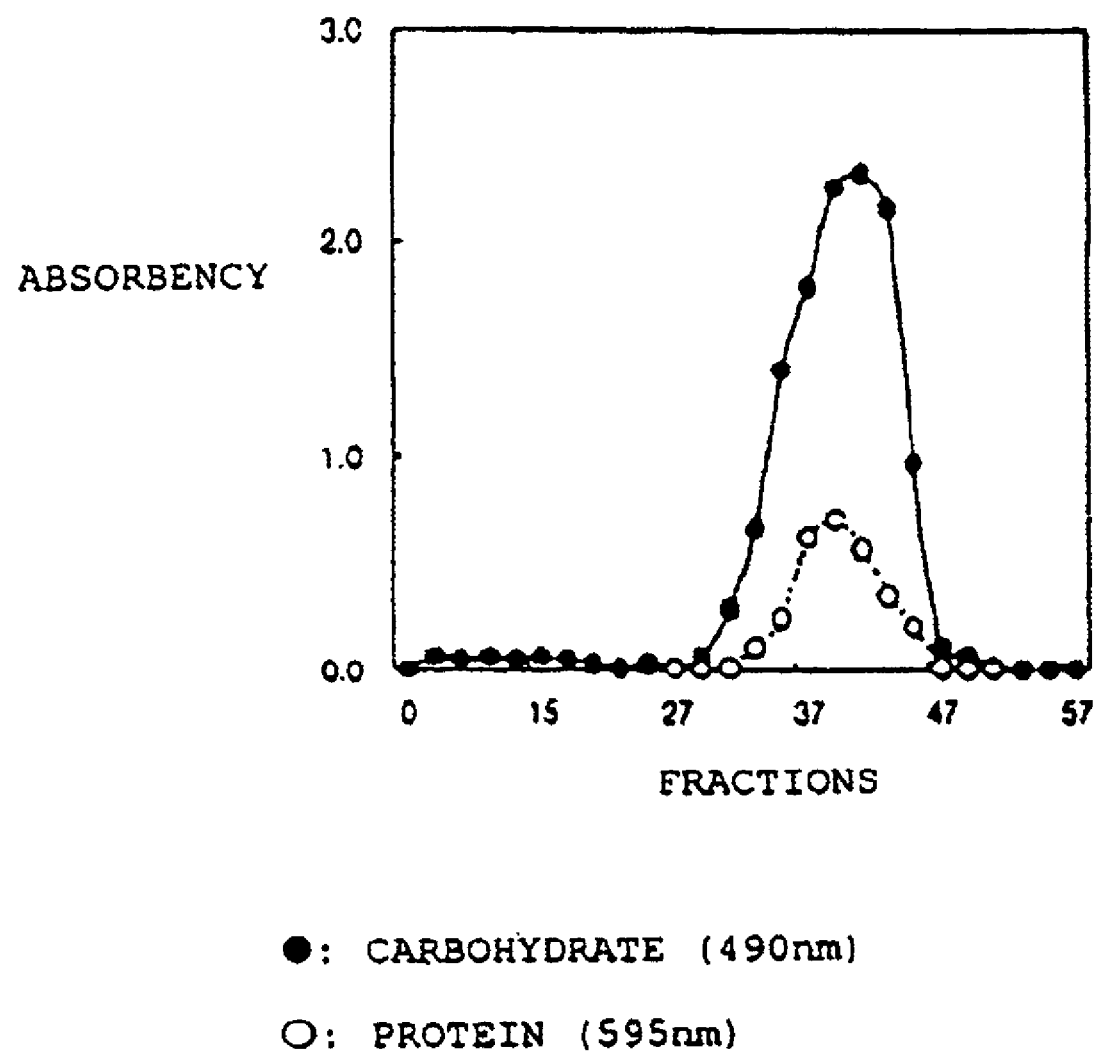
FIG. 5 is a HW 65F gel chromatogram for the immuno-stimulating polysaccharide substance.

First, its purity was confirmed by use of 65F gel column chromatography. FIG. 5 is the results of this chromatography. As seen, a single symmetric peak appeared for each carbohydrate and protein component, demonstrating that PL was pure.

Figure 6:
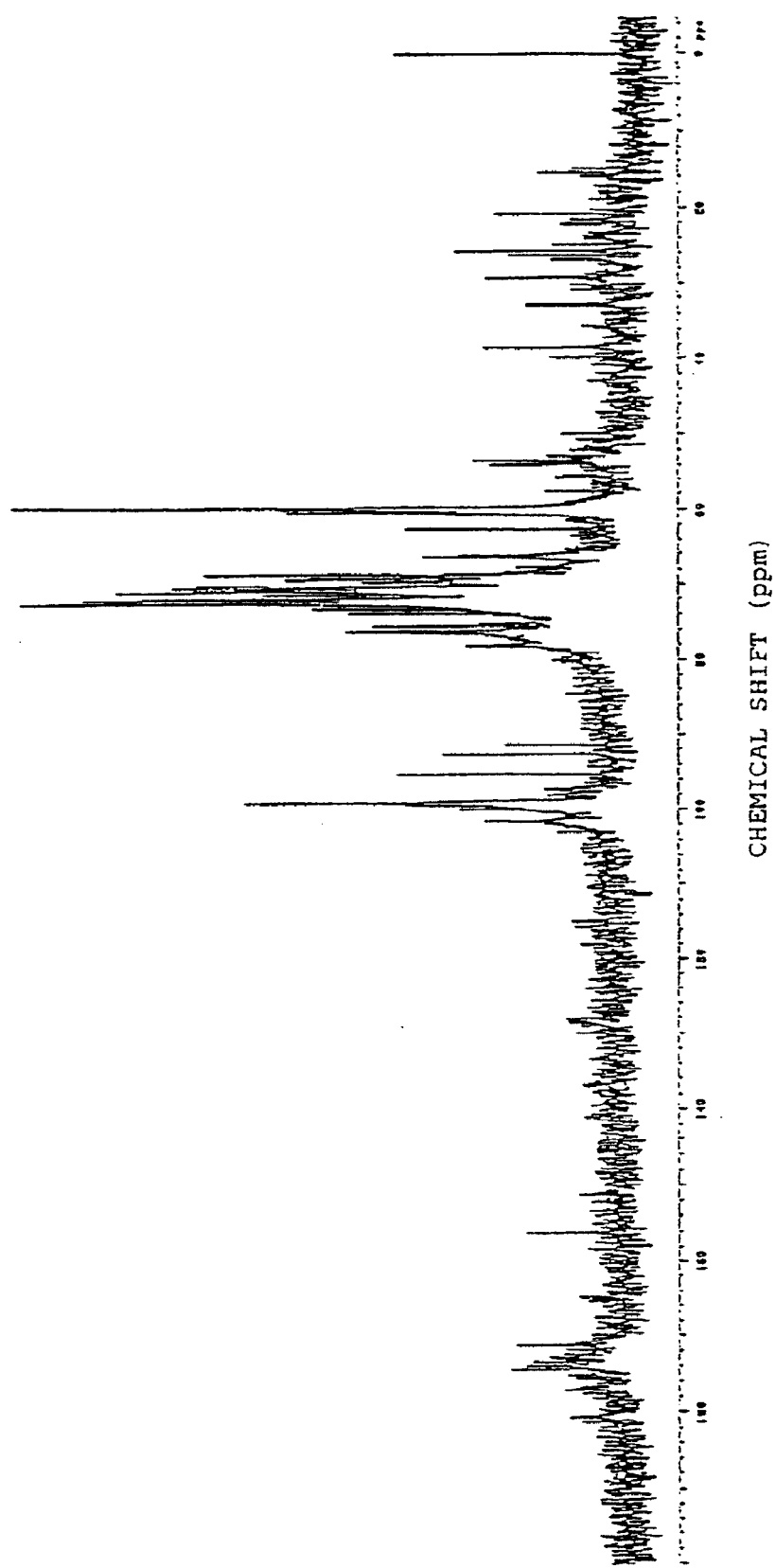
FIG. 6 is a carbon NMR spectrum for the immuno-stimulating polysaccharide substance.

From a carbon nuclear magnetic resonance spectrum (FIG. 6), PL was identified as a glactomannoglucan in which glucose units were joined by alpha(1→4) and β(1→6) linkages to form a long chain and mannose and galactoses were bonded as branches to the long chain.

This structural analysis accorded with the composition result, revealed that PL was a novel polysaccharide quite different in structure from β-glucan.

EXAMPLE XIV

Extraction of Polysaccharide Substances from Mycelia of *Phellinus* spp. Their Purification and Immuno-Stimulating Activity

*Phellinus* spp. strains, including *Phellinus igniarius, P. baumi, P. pini, P. gilvus* and *P. nigricans,* were cultured to obtain their mycelia. From them, polysaccharide substances were extracted and purified, and then, used to induce an enhancement in the cytotoxic function and antibody formation of the lymphocytes, B-cells and T-cells, as in Examples VIII to XI. Their anticancer immunoactivities were indirectly evaluated by counting the number of anti-forming lymphocytes and measuring the proliferation of T-cells. Obtained were similar results to those of Example XI.

EXAMPLE XV

Extraction of Polysaccharide Substances from Fruiting Bodies of *Phellinus* spp. Their Purification and Immuno-Stimulating Activity

*Phellinus* spp. strains, including *Phellinus igniarius, P. baumi, P. pini, P. gilvus* and *P. nigricans,* were cultured to obtain their fruiting bodies. From them, polysaccharide substances were extracted and purified, and then, used to induce an enhancement in the cytotoxic function and antibody formation of the lymphocytes, B-cells and T-cells, as in Examples VIII to XI. Their anticancer immunoactivities were indirectly evaluated by counting the number of anti-forming lymphocytes and measuring the proliferation of T-cells. Obtained were similar results to those of Example XI.

EXAMPLE XVI

Figure 7:
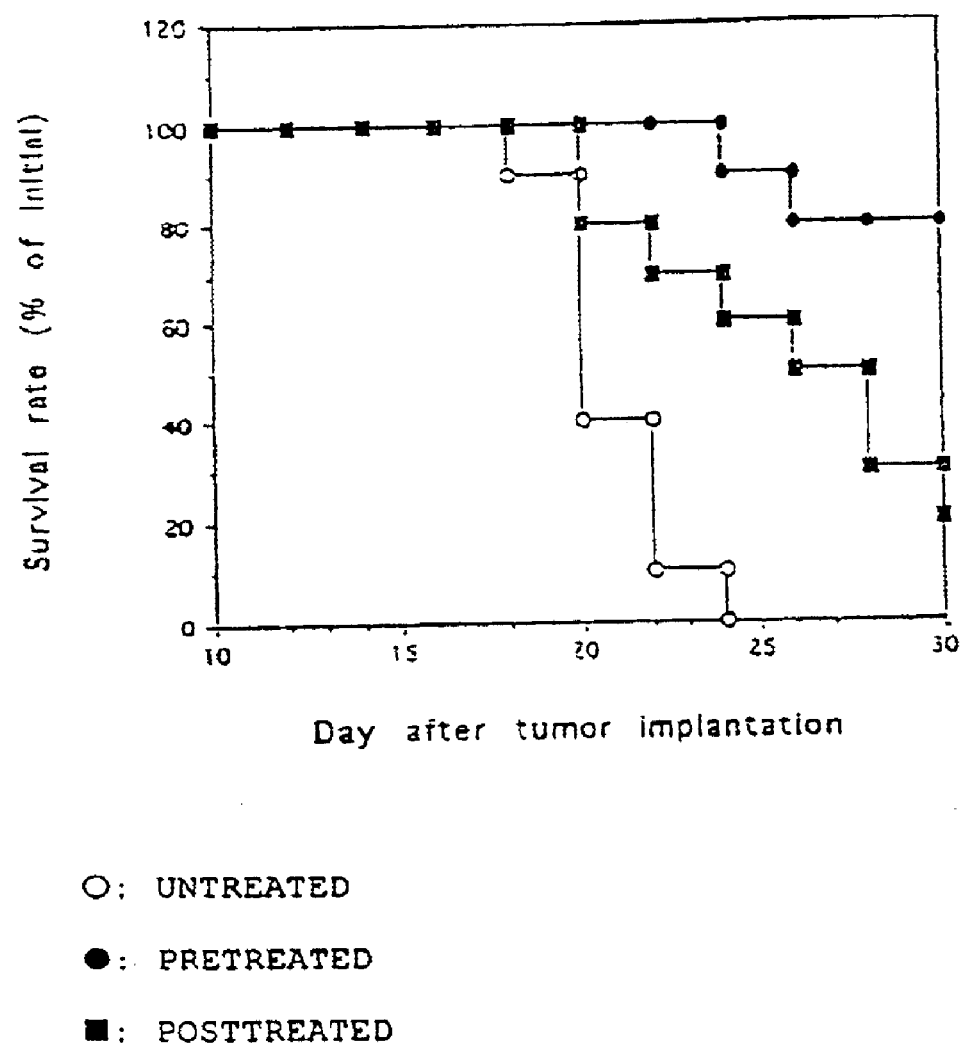
FIG. 7 is a graph showing the anticancer activities against mouse cancer cells of the polysaccharide substance according to administration manner.

Therapeutic Activity of the Polysaccharide Substance Against Cancer Cells According to Administration Time B16F10 cutaneous cancer cells, derived from mouse, were utilized for the measurement of the anticancer activity of the polysaccharide substance. B16F10 cutaneous cells were cultured in RPMI 1640 media supplemented with 10% serum and subcultured twice every week. As many as 100,000 cells of B16F10 per mouse were implanted in the peritoneal cavity. The mice implanted were recorded with respect to viability for 30 days. The recording was also performed for the mice which were peritoneally administrated with the polysaccharide substance from a week before the cancer cell implantation to 12 days after the implantation (pre-treatment) and for the mice which were peritoneally administrated with the polysaccharide substance for 12 days after the implantation (post-treatment). The results are given as shown in FIG. 7 and summarized in Table 12, below. As seen, the pre-treated mouse group was the highest in average viability, the post-treated mouse group next and the untreated mouse group is the lowest. The mice tested were not changed in body weight.

TABLE 12

Immunotherapy of the Polysaccharide Substance

| Test Groups (mg/kg) | Avg. Viability | Proportion (%) | Nos. of Viable Mice on the 30th day |
|---|---|---|---|
| Untreated | 20.8 | 100 | 0/10 |
| Pretreated (100) | 29.0 | 139 | 8/10 |
| Posttreated (100) | 25.8 | 124 | 2/10 |

EXAMPLE XVII

Activity of the Polysaccharide Substance Against Caner Cells According to Immunochemo Therapy Experiment 1: Anticancer Activity According to Co-Administration of the Polysaccharide Substance and Adriamycin A homogeneous plantation test system of B16F10 cutaneous cancer cell was utilized for the measurement of the anticancer activity upon co-administration of the polysaccharide substance and adriamycin. The cutaneous cancer cells were implanted in the peritoneal cavity of mice. Adriamycin was peritoneally administered to the mice for 12 days after tumor implantation while the polysaccharide substance was peritoneally administered from a week before the implantation to 12 days after the implantation. For 60 days, the viability of the mice was recorded everyday. Adriamycin was used at such low amounts as not to damage the mice.

Figure 8A:
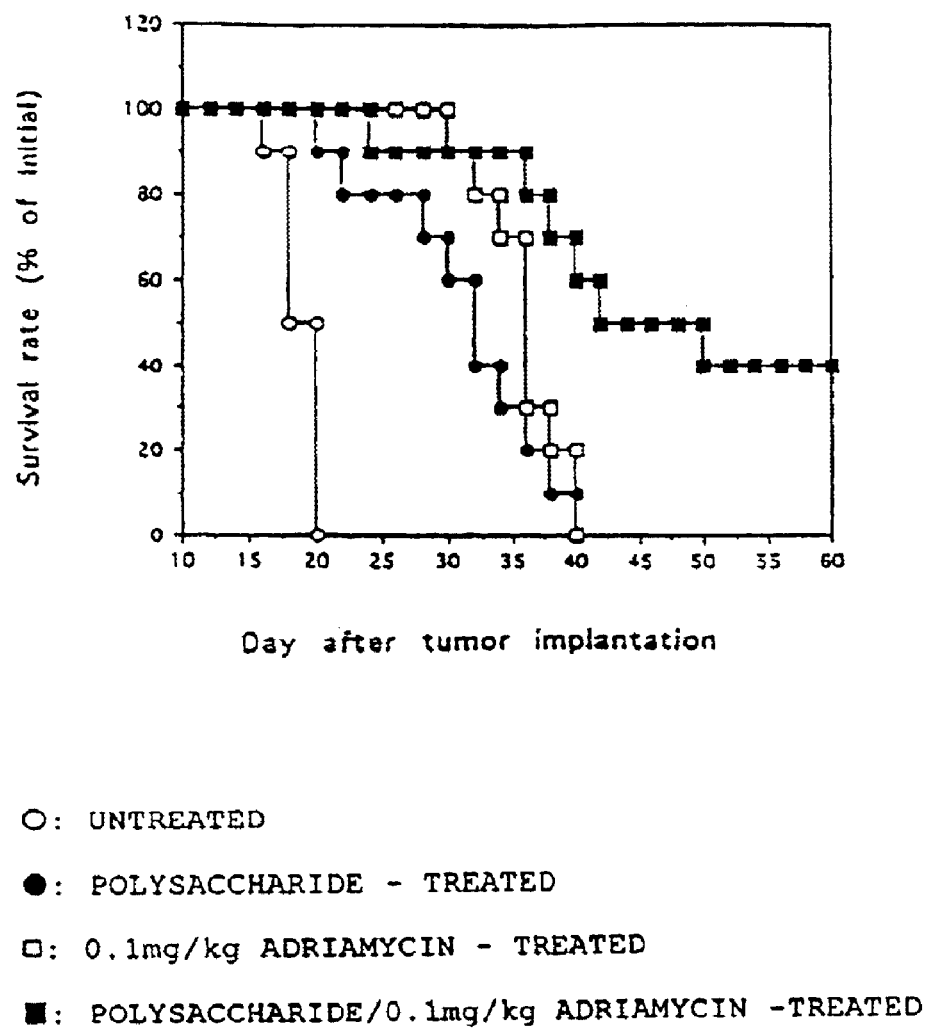
FIG. 8*a* is a graph showing the anticancer activities against mouse cancer cells of a combination of the polysaccharide substance and adriamycin 0.1 mg/kg.
Figure 8B:
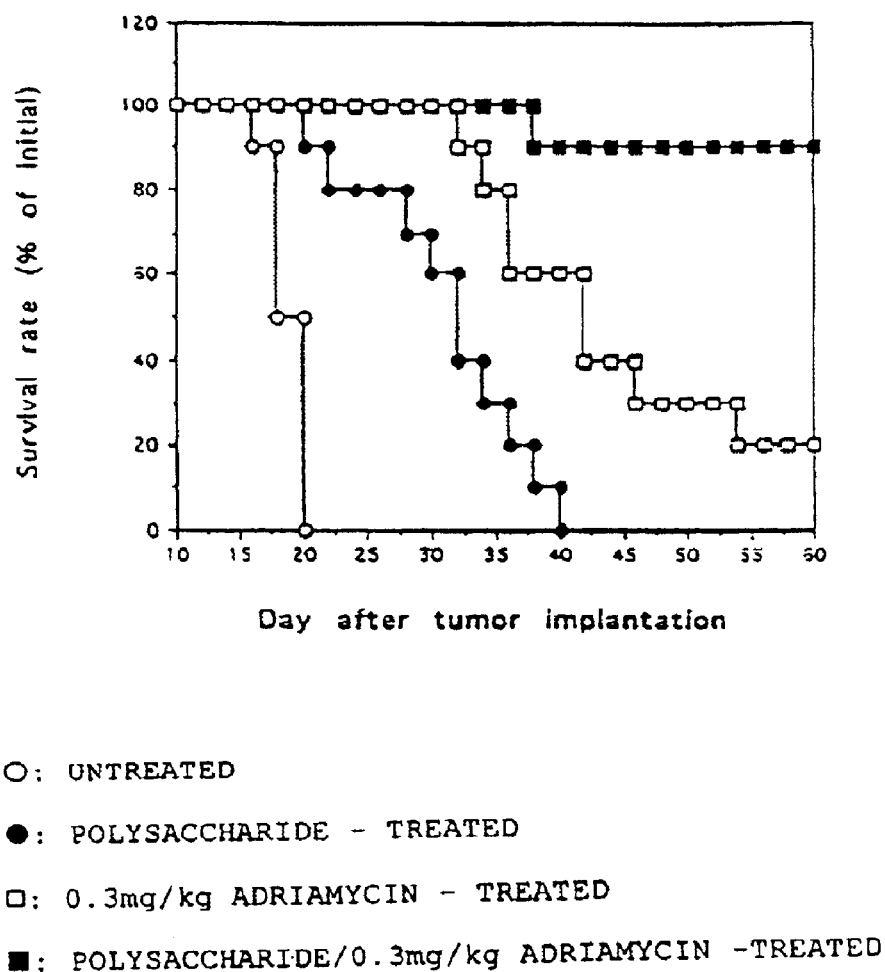
FIG. 8*b* is a graph showing the anticancer activities against mouse cancer cells of a combination of the polysaccharide substance and adriamycin 0.3 mg/kg.

The results are given as shown in FIGS. 8a and 8b and summarized in Table 13, below. As apparent from the data, the mice which were not treated with the agents, were very poor in viability and the mice which were treated with the polysaccharide substance alone were far superior in viability to the untreated mice. In FIGS. 8a and 8b, there are shown the results when adriamycin was administered at a dose of 0.1 mg and 0.3 mg per kg of body weight of a mouse, respectively. The viability was much better at a dose of 0.3 mg/kg than at 0.1 mg/kg. In the case of co-administration with the polysaccharide substance, adriamycin also more raised the mouse viability at a dose of 0.3 mg/kg than at 0.1 mg/kg. Numerically, the mice which were implanted with B16F10 cutaneous cancer cells were alive for 18.1 days in average. When they were treated with the polysaccharide substance alone, their average viability was extended to 31 days. Adriamycin allowed the mice to be alive for 35.4 days in average when being singly administered at a dose of 0.1 mg/kg while the mice could live 40.1 days in average by the sole administration of adriamycin at a dose of 0.3 mg/kg. Where adriamycin was administered in combination with the polysaccharide substance, the mice's average viability was significantly extended from 46.9 days at a dose of 0.1 mg/kg to 57.8 days at a dose of 0.3 mg/kg. During the test, the mice did not lose body weight.

TABLE 13

Immunotherapy of Combinations of Adriamycin and the Polysaccharide Substance

| Test Group (mg/kg) | Avg. Viability | Proportion (%) | Nos. of viable mice on the 60th day |
|---|---|---|---|
| Untreated | 18.1 | 100.0 | 0/10 |
| P.S[1] (100) | 31.0 | 171.3 | 0/10 |
| Am[2] (0.1) | 35.4 | 195.6 | 0/10 |
| Am (0.1) + P.S. (100) | 46.9 | 259.1 | 4/10 |
| Am (0.3) | 40.1 | 240.9 | 2/10 |
| Am (0.3) + P.S (100) | 57.8 | 319.3 | 9/10 |

[1] Polysaccharide Substance
[2] Adriamycin

Experiment 2: Anticancer Activity According to Co-Administration of the Polysaccharide Substance and Mitomycin C A homogeneous plantation test system of B16F10 cutaneous cancer cell was utilized for the measurement of the anticancer activity upon co-administration of the polysaccharide substance and mitomycin C, as in Experiment 1. The cutaneous cancer cells were implanted in the peritoneal cavity of mice. Mitomycin C was peritoneally administered to the mice for 12 days after tumor implantation while the polysaccharide substance was peritoneally administered from a week before the implantation to 12 days after the implantation. For 60 days, the viability of the mice was recorded everyday. Mitomycin C was used at such low amounts as not to damage the mice.

Similar results to those of Experiment 1 were obtained and are summarized in Table 14, below. As apparent from the data, the mice which were not treated with the agents, were very poor in viability and the mice which were treated with the polysaccharide substance alone were far superior in viability to the untreated mice. Numerically, the mice which were implanted with B16F10 cutaneous cancer cells were alive for 18.1 days in average, but when they were treated with the polysaccharide substance alone, their average viability was extended to 31 days. mitomycin C allowed the mice to be alive for 32.5 days in average when being singly administered at a dose of 0.2 mg/kg while the mice could live 38.0 days in average by the sole administration of mitomycin C at a dose of 0.6 mg/kg. Where mitomycin C was administered in combination with the polysaccharide substance, the mice's average viability was significantly extended from 43.5 days at a dose of 0.2 mg/kg to 51.5 days at a dose of 0.6 mg/kg. During the test, the mice did not lose body weight.

TABLE 14

Immunotherapy of Combinations of Mitomycin C and the Polysaccharide Substance

| Test Group (mg/kg) | Avg. Viability | Proportion (%) | Nos. of viable mice on the 60th day |
|---|---|---|---|
| Untreated | 18.1 | 100.0 | 0/10 |
| P.S[1] (100) | 31.0 | 171.3 | 0/10 |
| M.C[2] (0.2) | 32.5 | 179.6 | 0/10 |
| M.C (0.2) + P.S (100) | 43.5 | 240.3 | 3/10 |

TABLE 14-continued

Immunotherapy of Combinations of Mitomycin C and the Polysaccharide Substance

| Test Group (mg/kg) | Avg. Viability | Proportion (%) | Nos. of viable mice on the 60th day |
|---|---|---|---|
| M.C (0.6) | 38.0 | 209.9 | 1/10 |
| M.C (0.6) + P.S (100) | 51.5 | 284.5 | 7/10 |

[1]polysaccharide substance
[2]Mitomycin C

Experiment 3: Anticancer Activity According to Co-Administration of the Polysaccharide Substance and Cisplatin A homogeneous plantation test system of B16F10 cutaneous cancer cell was utilized for the measurement of the anticancer activity upon co-administration of the polysaccharide substance and cisplatin, as in the above experiments. The cutaneous cancer cells were implanted in the peritoneal cavity of mice. Cisplatin was peritoneally administrated to the mice for 12 days after tumor implantation while the polysaccharide substance was peritoneally administrated from a week before the implantation to 12 days after the implantation. For 60 days, the viability of the mice was recorded everyday. Cisplastin was used at such low amounts as not to damage the mice.

Similar results to those of the above experiments were obtained and are summarized in Table 15, below. As apparent from the data, the mice which were not treated with the agents, were very poor in viability and the mice which were treated with the polysaccharide substance alone were far superior in viability to the untreated mice. Numerically, the mice which were implanted with B16F10 cutaneous cancer cells were alive for 18.1 days in average, but when they were treated with the polysaccharide substance alone, their average viability was extended to 31 days. Cisplatin allowed the mice to be alive for 33 days in average when being singly administrated at a dose of 0.5 mg/kg while the mice could live 40.5 days in average by the sole administration of cisplatin at a dose of 1.5 mg/kg. Where cisplatin was administrated in combination with the polysaccharide substance, the mice's average viability was significantly extended from 44.0 days at a dose of 0.5 mg/kg to 52.6 days at a dose of 1.5 mg/kg. During the test, the mice did not lose body weight.

TABLE 15

Immunotherapy of Combinations of Cisplatin and the Polysaccharide Substance

| Test Group (mg/kg) | Avg. Viability | Proportion (%) | Nos. of viable mice on the 60th day |
|---|---|---|---|
| Untreated | 18.1 | 100.0 | 0/10 |
| P.S[1] (100) | 31.0 | 171.3 | 0/10 |
| C.P[2] (0.5) | 33.0 | 182.3 | 0/10 |
| C.P (0.5) + P.S (100) | 44.0 | 243.0 | 3/10 |
| C.P (1.5) | 40.5 | 223.8 | 2/10 |
| C.P (1.5) + P.S (100) | 52.6 | 290.6 | 7/10 |

[1]Polysaccharide Substance
[2]Cisplatin

Experiment 4: Anticancer Activity According to Co-Administration of the Polysaccharide Substance and 5-fluoro Uracil A homogeneous plantation test system of B16F10 cutaneous cancer cell was utilized for the measurement of the anticancer activity upon co-administration of the polysaccharide substance and 5-fluoro uracil, as in the above experiments. The cutaneous cancer cells were implanted in the peritoneal cavity of mice. 5-fluoro uracil was peritoneally administrated to the mice for 12 days after tumor implantation while the polysaccharide substance was peritoneally administrated from a week before the implantation to 12 days after the implantation. For 60 days, the viability of the mice was recorded everyday. 5-fluoro uracil was used at such low amounts as not to damage the mice.

Similar results to those of the above experiments were obtained and are summarized in Table 16, below. As apparent from the data, the mice which were not treated with the agents were very poor in viability and the mice which were treated with the polysaccharide substance alone were far superior in viability to the untreated mice. Numerically, 5-Fluoro uracil allowed the mice to be alive for 34.2 days in average when being singly administrated at a dose of 1 mg/kg and for 45.5 days in average when being administrated in combination with the polysaccharide substance. A dose of 3 mg/kg of 5-fluoro uracil enabled the mice to live 40.2 days in average when being administrated alone and to live 54.8 days in average when being administrated together with the polysaccharide substance. During the test, the mice did not lose body weight.

TABLE 16

| Test Group (mg/kg) | Avg. Viability | Proportion (%) | Nos. of viable mice on the 60th day |
|---|---|---|---|
| Untreated | 18.1 | 100.0 | 0/10 |
| P.S[1] (100) | 31.0 | 171.3 | 0/10 |
| 5-FU[2] (1) | 33.0 | 187.8 | 0/10 |
| 5-FU (1) + P.S (100) | 44.0 | 251.4 | 4/10 |
| 5-FU (3) | 40.5 | 222 | 2/10 |
| 5-FU (3) + P.S (100) | 52.6 | 302.0 | 8/10 |

[1]Polysaccharide Substance
[2]Fluorouracil

EXAMPLE XVIII

Activity of the Polysaccharide Substance Against Cancer Cells Derived from the Human Body The activity of the polysaccharide substance against human cancer was assayed using NCl-H23, a lung cancer cell line. Nude mice were subcutaneously implanted with NCl-H23 lung cancer cells. The polysaccharide substance and adriamycin were peritoneally administrated to the nude mice for 12 days after cancer cell implantation. The size of a mass of the cancer cells was measured and the cancer cells were separated and weighed on the 19th day after cancer cell implantation. Because the nude mice were devoid of T-cells, their immunological competency was generally attributed to the activity of natural killer cells or macrophage cells. Therefore, the immunological enhancement obtained when administrating the polysaccharide substance was meditated through these two type cells.

Figure 9A:
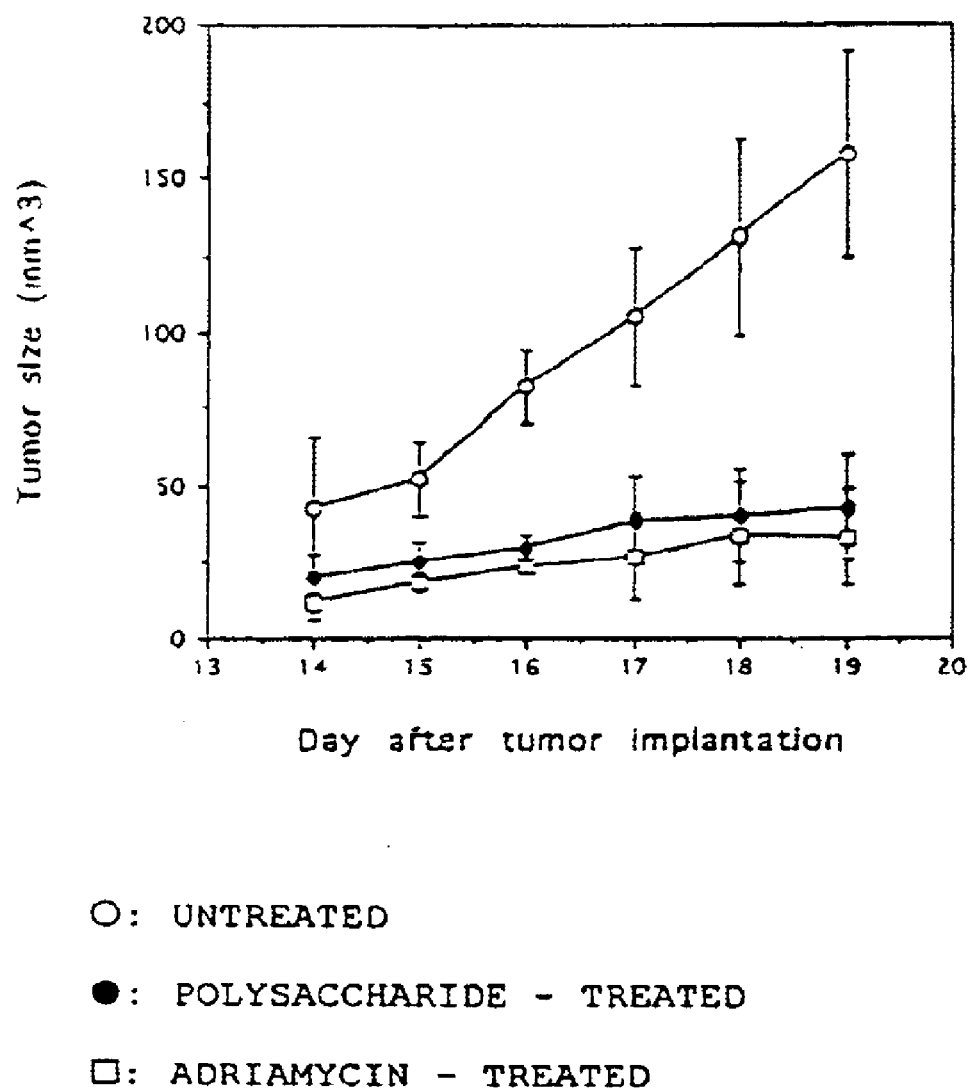
FIG. 9*a* is a graph showing the change of the human cancer cells according to the treatment with the polysaccharide substance and adriamycin.
Figure 9B:
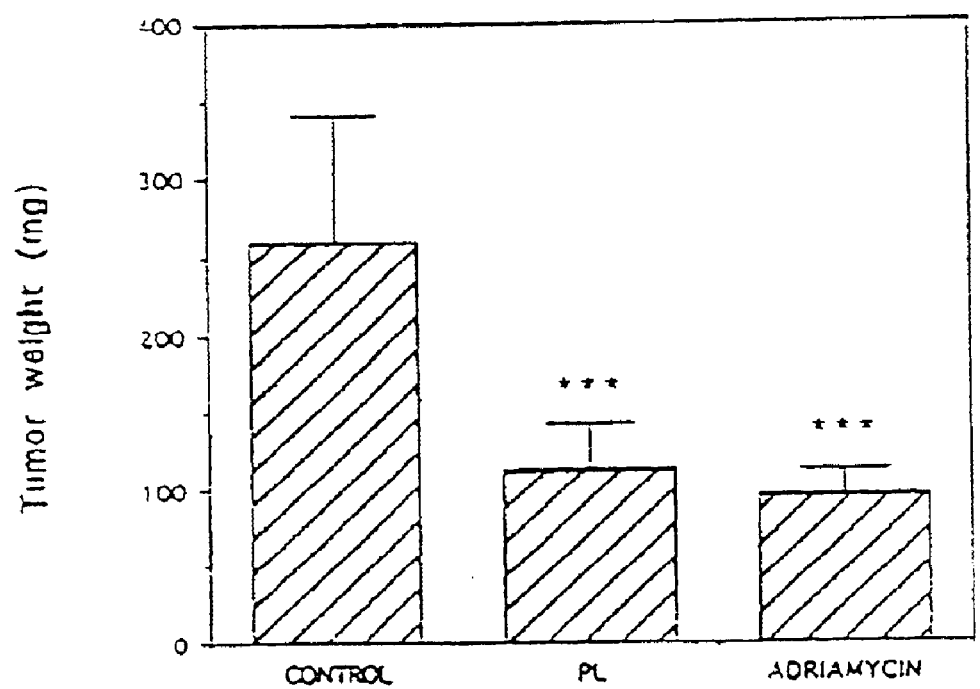
FIG. 9*b* is a graph showing the final weight of the human cancer cells according to the treatment with the polysaccharide substance and adriamycin.

The results are given as shown in FIGS. 9a and 9b and numerically listed in Tables 17 and 18, below. As apparent from these data, the cancer cells which were treated with neither adriamycin nor the polysaccharide substance was the largest in size, the polysaccharide substance-treated cancer cells next, and the adriamycin-treated cancer cells the smallest. For weight, the same order resulted in. The tested mice did not gain or lose body weight.

TABLE 17

Immunotherapy for Human Cancer Cells
(Cell size mm³)

| Test group | 14th day | 17th day | 18th day | 19th day |
|---|---|---|---|---|
| Untreated | 43 | 105 | 131 | 158 |
| P.S¹ (100 mg/kg) | 20 | 39 | 40 | 43 |
| Am² (1 mg/kg) 12 | 27 | 34 | 33 | |

¹Polysaccharide Substance
²Adriamycin

TABLE 18

Immunotherapy for Human Cancer Cells

| Test Group | Final Cancer Weight |
|---|---|
| untreated | 259 |
| P.S¹ (100 mg/kg) | 113 |
| Adriamycin (1 mg/kg) | 95 |

¹Polysaccharide Substance

EXAMPLE XIX

Effect of the Polysaccharide Substance on Metastasis of Mouse Cancer Cells

Figure 10A:
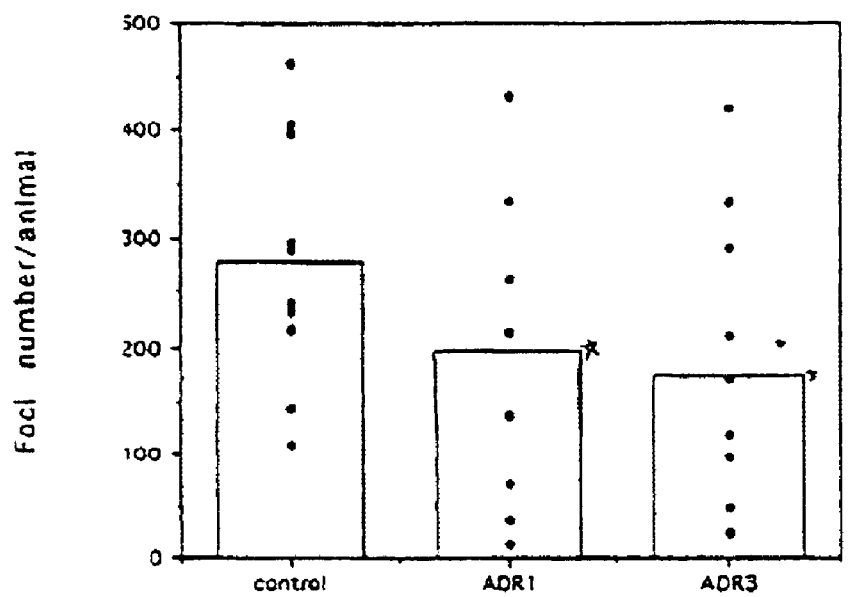
FIG. 10*a* is a graph showing a prevention effect of adriamycin on cancer metastasis.
Figure 10B:
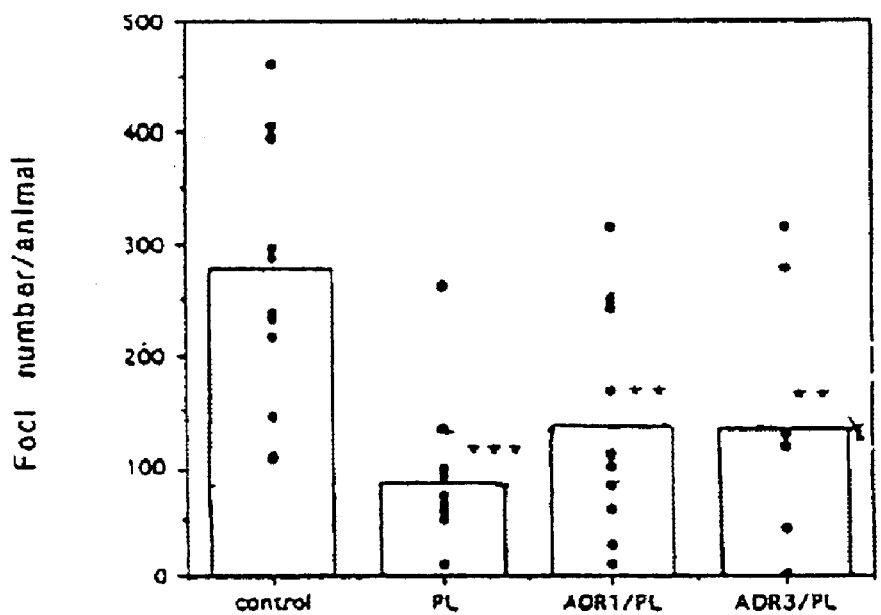
FIG. 10*b* is a graph showing a prevention effect of a combination of the polysaccharide substance and adriamycin on cancer metastasis.

In order to test the polysaccharide substance for the prevention of cancer metastasis, B16F10 cutaneous cancer cells were implanted in the tail veins of C57BL/6 mice. On the 14th day after implantation, the lungs were isolated from the mice to investigate whether or to what extent cancer metastasis occurred. Adriamycin was peritoneally administrated to the mice for 12 days after tumor implantation while the polysaccharide substance was peritoneally administrated from a week before the implantation to 12 days after the implantation. The B16F10 cutaneous cancer cells injected intravenously to the tails were translocated to form black spots on the lungs. The results are given as shown in FIGS. 10a and 10b and numerically summarized in Table 19, below. As shown in FIG. 10a, as many as about 272 cancer spots were found in the mouse group which was not treated with any agents and they were reduced to 197 when administrating adriamycin at a dose of 1 mg/kg and further reduced to 172 when administrating adriamycin at a dose of 3 mg/kg. Adriamycin at a dose of 0.1–0.3 mg/kg showed a potent activity of preventing cancer cells from growing, but it showed only a very weak effect on the prevention of cancer metastasis event at a dose of 1–3 mg/kg. The number of the cancer spots was reduced to 83 by administrating the polysaccharide substance alone. 136 and 131 cancer spots were found in the mouse groups which were administrated with the polysaccharide substance in combination with adriamycin at a dose of 1 mg/kg and 3 mg/kg, respectively. Therefore, the polysaccharide substance is more effective for the prevention of cancer metastasis than adriamycin.

TABLE 19

| Test Group | Nos. of Spots |
|---|---|
| Untreated | 272 |
| P.S¹ (100 mg/kg) | 83 |
| Adriamycin (1 mg/kg) | 197 |
| Adriamycin (1 mg/kg) + P.S (100 mg/kg) | 136 |
| Adriamycin (3 mg/kg) | 172 |
| Adriamycin (3 mg/kg) + P.S (100 mg/kg) | 131 |

¹Polysaccharide Substance

EXAMPLE XX

Test for Direct Cytotoxicity of the Polysaccharide Substance to Caner Cells

Figure 11:
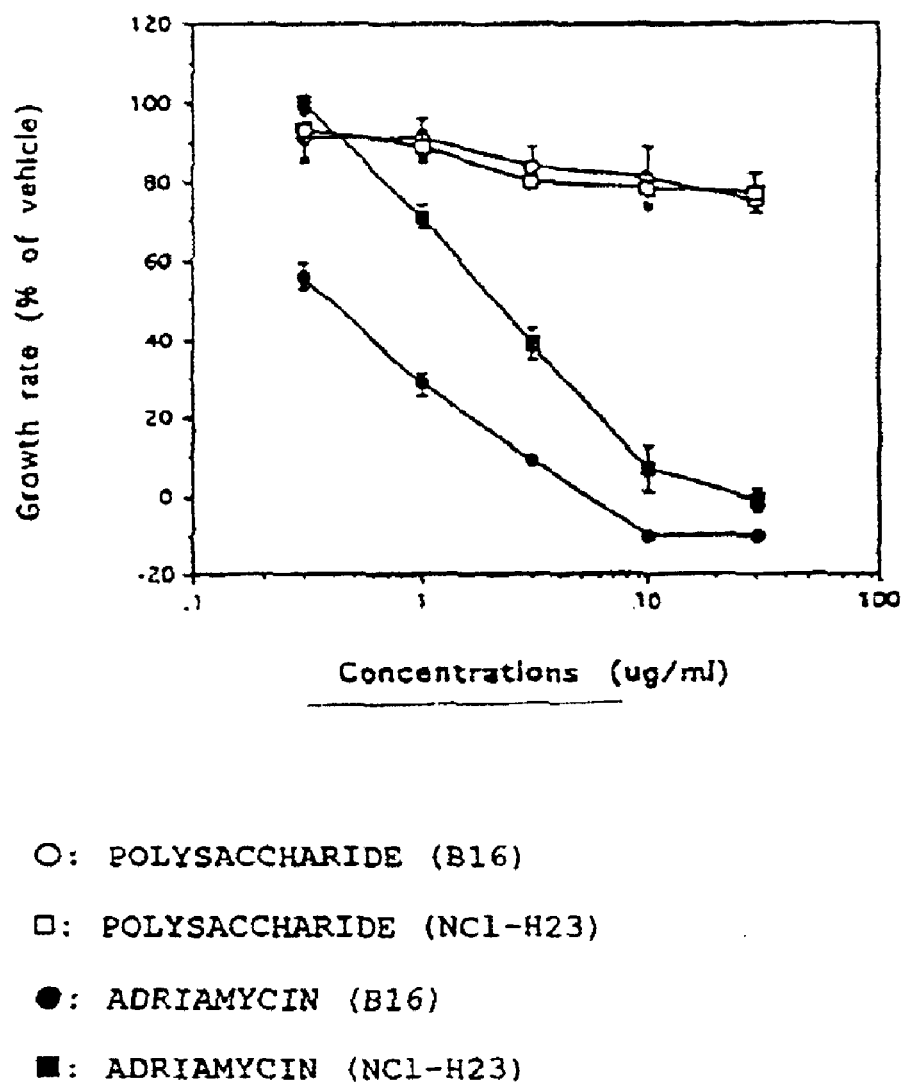
FIG. 11 is a graph showing the cytotoxicity of adriamycin and polysaccharide substance.

The anticancer activity of the polysaccharide substance was tested for whether it is expressed through immunological enhancement or by direct cytotoxicity to cancer cells. B16F10 mouse cutaneous cancer cells and NCl-H23 human lung cancer cells were directly treated with the polysaccharide substance and adriamycin at an amount of 0.3–30 μg/kg. The cancer cells still alive on the 2nd day after treatment were measured according to a sulforhodamin B method. The results are given as shown in FIG. 11 and numerically summarized in Table 20, below. The cell quantity of the test groups which were not treated with any chemicals was expressed as "100%" and the cell quantities of treated test groups were compared with this standard. As apparent from the data, adriamycin exhibits potent cytotoxicity to the two type cancer cells while the polysaccharide substance does not. Taken together, the data obtained in the above examples show that adriamycin exerts anticancer activity through cytotoxicity while the polysaccharide substance displays anticancer activity through the immunological enhancement.

TABLE 20

Direct Cytotoxicity of the Polysaccharide Substance

| | Adriamycin | | Polysaccharide Substance | |
|---|---|---|---|---|
| Test Group | B16F10 | NCl-H23 | B16F10 | NCl-H23 |
| Untreated | 100 | 100 | 100 | 100 |
| 0.3 μg/mL | 56 | 100 | 93 | 93 |
| 1 μg/mL | 29 | 71 | 89 | 89 |
| 3 μg/mL | 9 | 39 | 80 | 80 |
| 10 μg/ml | −10 | 7 | 78 | 78 |
| 30 μg/mL | −10 | −1 | 77 | 77 |

EXAMPLE XXI

Test for Use as an Aid in Prophylaxis and Treatment of AIDS

The polysaccharide substance according to the present invention was tested for the availability of an aid for the prophylaxis and treatment of AIDS and found to be effective therefor.

Taken together, the data of the Examples show that the mushroom of the present invention is a novel strain with a relatedness to *Phellinus* spp. as analyzed by RFLP and the polysaccharide substance obtained from the mycelia of *Phellinus* spp. has an anticancer activity by inciting the cytotoxicity of T-cells and the antibody forming potency of B-cells. In addition, the polysaccharide substance of the present invention shows a potent activity against cancer metastasis. Consequently, the polysaccharide substance, which can stimulate the immunity of the body, may be effective in the prophylaxis and treatment of immune-related diseases, such as cancers and AIDS and thus, is very useful in the biomedical industry.

The present invention has been described in an illustrative manner, and it is to be understood the terminology used is intended to be in the nature of description rather than of limitation.

Many modifications and variations of the present invention are possible in light of the above teachings. Therefore, it is to be understood that within the scope of the appended claims, the invention may be practiced otherwise than as specifically described.

What is claimed is:

1. A biologically pure culture of *Phellinus linteus* strain KCTC 0399BP, which produces an immuno-stimulating substance, consisting of 82.7% carbohydrate and 17.3% protein, wherein the carbohydrate consists of glucose, mannose and galactose and wherein the glucose units are joined by $\alpha(1\to4)$ and $\beta(1\to6)$ linkages to form a chain and the mannose and the galactose are bonded as branches to the chain.

2. A biologically pure culture of *Phellinus linteus* strain KCTC 0399BP.

3. The biologically pure culture of claim 1, wherein the carbohydrate consists of 78.6 mole % glucose, 18.0 mole % mannose, and 3.4 mole % galactose.

4. The biologically pure culture of claim 1, which produces the immuno-stimulating substance when cultured in a culture broth at a pH of 6.0 and a temperature of 28° C. for 5 days.

5. The biologically pure culture of claim 4, wherein the culture broth contains 50 g starch, 10 g peptone, 10 g yeast extract, 0.8 g $KH_2PO_4$, 0.5 g $MgSO_4\cdot7H_2O$ and 0.3 g $CaCl_2$ per 1 L of distilled water.

* * * * *